US012623992B2

(12) United States Patent
Ding et al.

(10) Patent No.: US 12,623,992 B2
(45) Date of Patent: May 12, 2026

(54) KEY INTERMEDIATE FOR SYNTHESIS OF PROSTAGLANDIN COMPOUND AND PREPARATION METHOD THEREOF

(71) Applicant: SHENZHEN CATALYS TECHNOLOGY CO., LTD, Shenzhen (CN)

(72) Inventors: Xiaobing Ding, Hangzhou (CN); Qiwei Lang, Hangzhou (CN); Wei Su, Hangzhou (CN); Shuang Gao, Hangzhou (CN)

(73) Assignee: SHENZHEN CATALYS TECHNOLOGY CO., LTD, Shenzhen (CN)

( * ) Notice: Subject to any disclaimer, the term of this patent is extended or adjusted under 35 U.S.C. 154(b) by 762 days.

(21) Appl. No.: 17/680,362

(22) Filed: Feb. 25, 2022

(65) Prior Publication Data

US 2022/0281797 A1 Sep. 8, 2022

Related U.S. Application Data

(63) Continuation of application No. PCT/CN2021/117634, filed on Sep. 10, 2021.

(30) Foreign Application Priority Data

Sep. 16, 2020 (CN) ......................... 202010978194.8

(51) Int. Cl.

| | |
|---|---|
| ***C07C 59/48*** | (2006.01) |
| ***C07C 33/025*** | (2006.01) |
| ***C07C 33/20*** | (2006.01) |
| ***C07C 43/23*** | (2006.01) |
| ***C07C 49/757*** | (2006.01) |
| ***C07C 59/46*** | (2006.01) |
| ***C07D 307/935*** | (2006.01) |
| ***C07D 317/12*** | (2006.01) |
| ***C07F 7/18*** | (2006.01) |

(52) U.S. Cl.

CPC ............ *C07C 59/48* (2013.01); *C07C 33/025* (2013.01); *C07C 33/20* (2013.01); *C07C 43/23* (2013.01); *C07C 49/757* (2013.01); *C07C 59/46* (2013.01); *C07D 307/935* (2013.01); *C07D 317/12* (2013.01); *C07F 7/1804* (2013.01); *C07C 2601/08* (2017.05)

(58) Field of Classification Search

CPC ...................................................... C07C 59/48

See application file for complete search history.

(56) References Cited

U.S. PATENT DOCUMENTS 5,599,837 A 2/1997 Kishi et al.

OTHER PUBLICATIONS

Zhang, Fuhao et al. "Concise, scalable and enantioselective total synthesis of prostaglandins." Nature Chemistry. vol. 13 (Jul. 2021), pp. 692-697. (Year: 2021).*

American Chemical Society. Chemical Abstract Service. RN 2649250-97-3. Entered into STN: Jun. 30, 2021. (Year: 2021).*

American Chemical Society. Chemical Abstract Service. RN 37752-08-2. Entered into STN: Nov. 16, 1984. (Year: 1984).*

(Continued)

*Primary Examiner* — John S Kenyon

(74) *Attorney, Agent, or Firm* — JEEN IP LAW, LLC

(57) ABSTRACT

The present invention relates to the technical field of organic chemical engineering, and in particular to a key intermediate for synthesizing prostaglandin compounds and a preparation method therefor. When applied to the synthesis of prostaglandin compounds, the process flow is simplified, the yield and product purity are improved, the production costs are reduced, and the industrial application is easy.

I

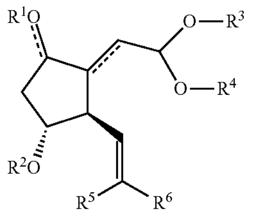

or

II

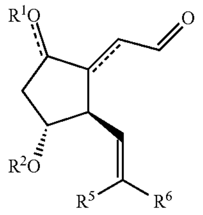

or

III

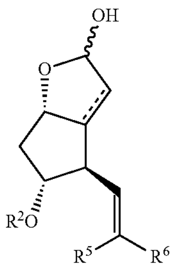

12 Claims, 1 Drawing Sheet

(56) References Cited

OTHER PUBLICATIONS

Josef Fried et al. Stereospecific Total Synthesis of the Natural and Racemic Prostaglandins of the E and F Series «Journal of the American Chemical Society» Jun. 14, 1972 (Jun. 14, 1972) No. 12 vol. 94 ISSN: 0002-7863 pp. 4342-4343.

Taehyeong Kim et al. Total synthesis of PGF2α and 6,15-diketo-PGF1α and formal synthesis of 6-keto-PGF1α via three-component coupling «Tetrahedron» Sep. 10, 2019 (Sep. 10, 2019) No. 42 vol. 75 ISSN:0040-4020 p. 130593 (1-9).

* cited by examiner

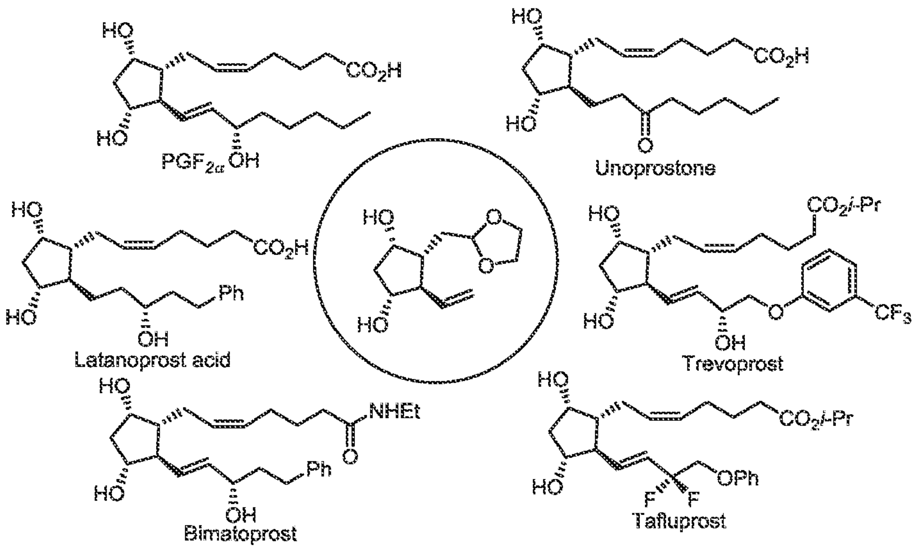
PGF$_{2\alpha}$
Unoprostone
Latanoprost acid
Trevoprost
Bimatoprost
Tafluprost

KEY INTERMEDIATE FOR SYNTHESIS OF PROSTAGLANDIN COMPOUND AND PREPARATION METHOD THEREOF

TECHNICAL FIELD

The present invention relates to the technical field of organic chemical engineering, and particularly to a key intermediate for the synthesis of a prostaglandin compound and a preparation method thereof.

BACKGROUND

Prostaglandins are a class of important endogenous products with a variety of physiological activities, and many derivatives obtained therefrom by modifying their structures also have important physiological activities. At present, a number of compounds are available in the market for the treatment of glaucoma, ulcer, early pregnancy, constipation and high blood pressure and the like. The prostaglandin compounds include, but are not limited to,

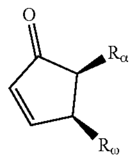

PGA

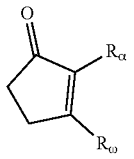

PGB

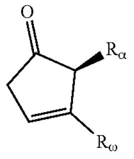

PGC

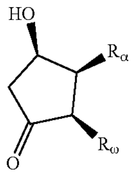

PGD

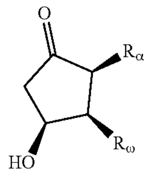

PGE

-continued

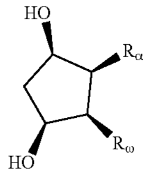

$PGF_a$

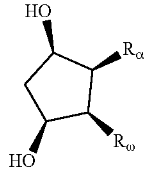

$PGF_\beta$

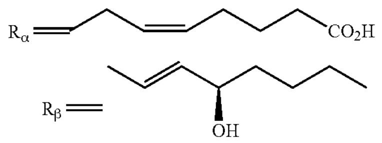

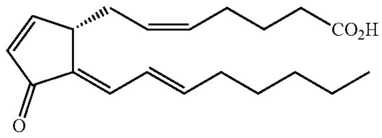

$PGJ_2$

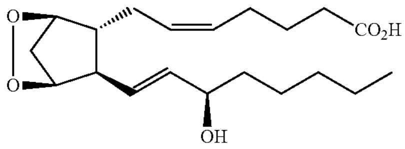

$PGH_2$

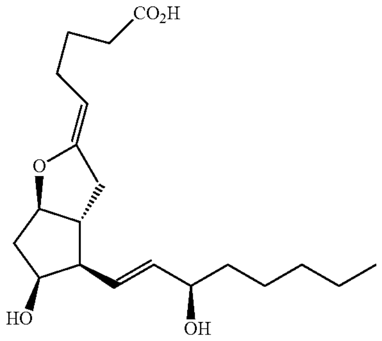

$PGI_2$

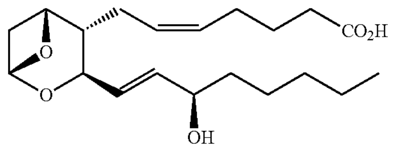

$TXA_2$

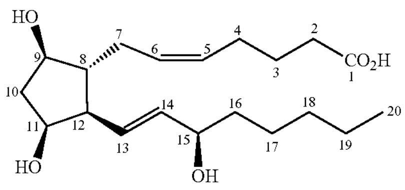

$PGF_{2\alpha}$

-continued
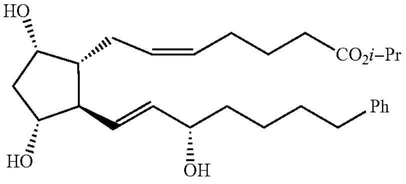
Latanoprost
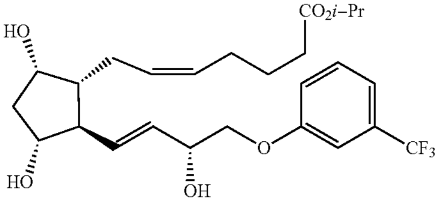
Trevoprost
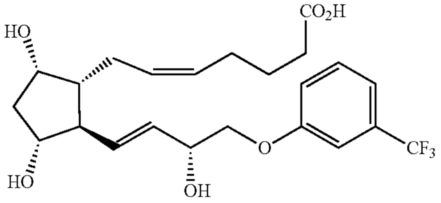
Fluprostenol
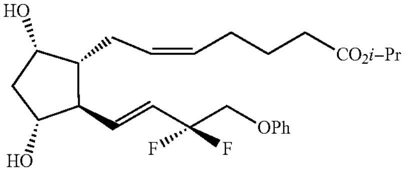
Tafluprost
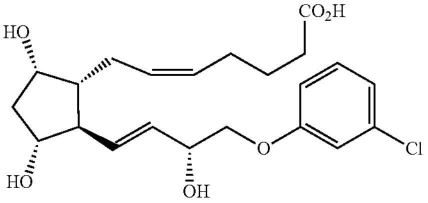
Cloprostenol
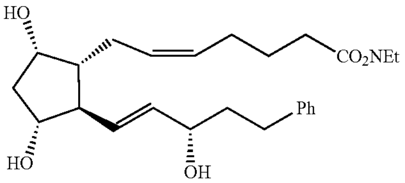
Blmatoprost
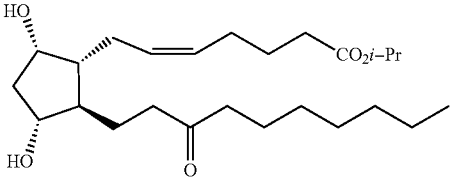
Unoprostone isopropyl ester
-continued
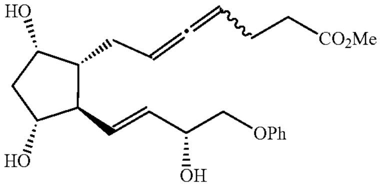
(±)-Fenprostaiene
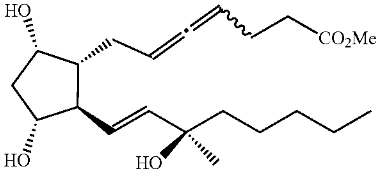
Prostalene
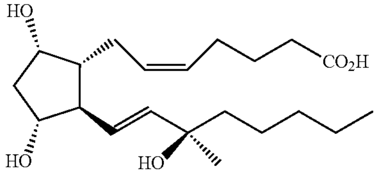
Carboprost
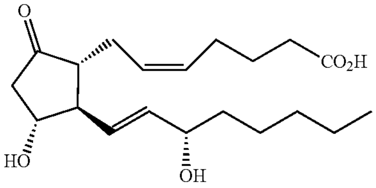
Dinoprostone
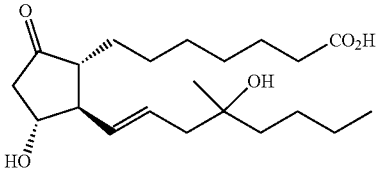
Misoprostol
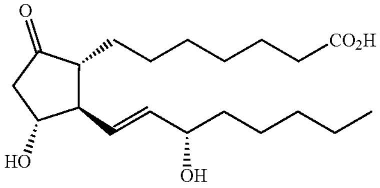
Alprostadl (PGE1)
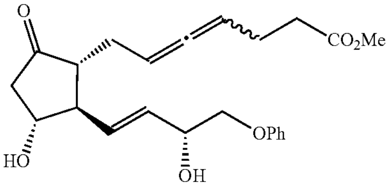
(±)Enprostil -continued
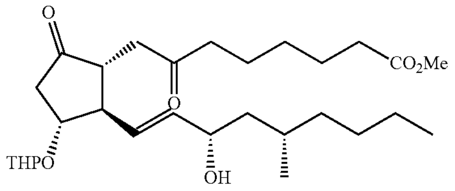
Omoprostol
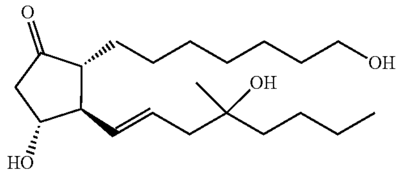
Rioprostol
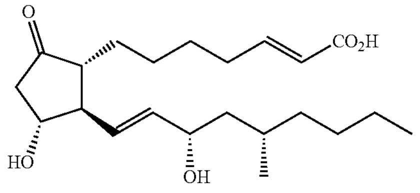
Limaprost
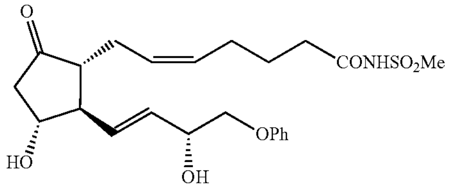
Sulprostone
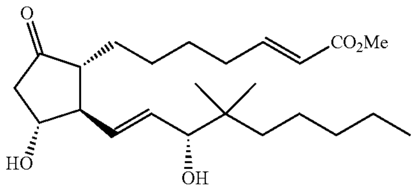
Gameprost
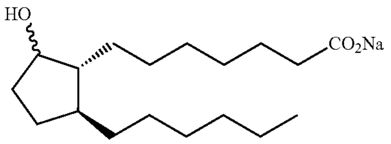
Rosaprostol
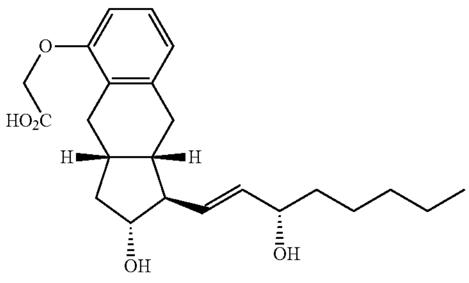
Treprostinil
-continued
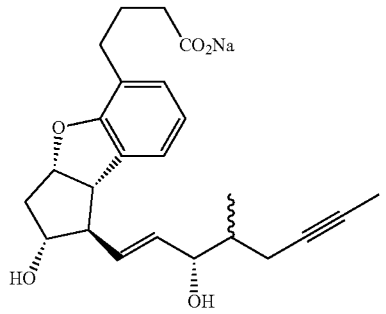
Beraprost
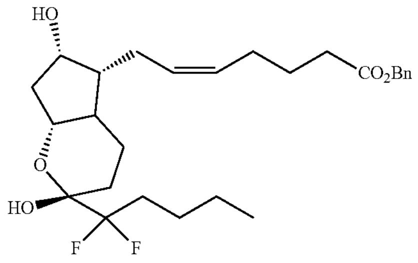
Lubiprostone
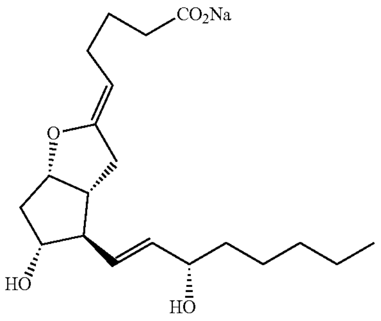
Epoprostenol
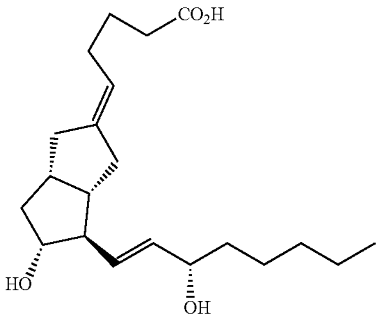
Carbacyclin
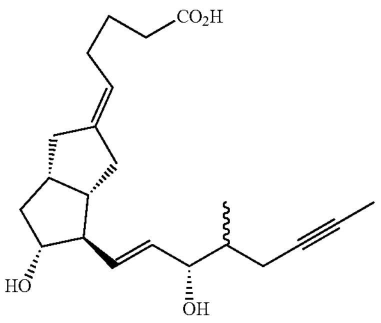
Iloprost The synthetic routes for preparing the aforementioned compounds in the prior art mainly include:
Scheme 1. Corey's route
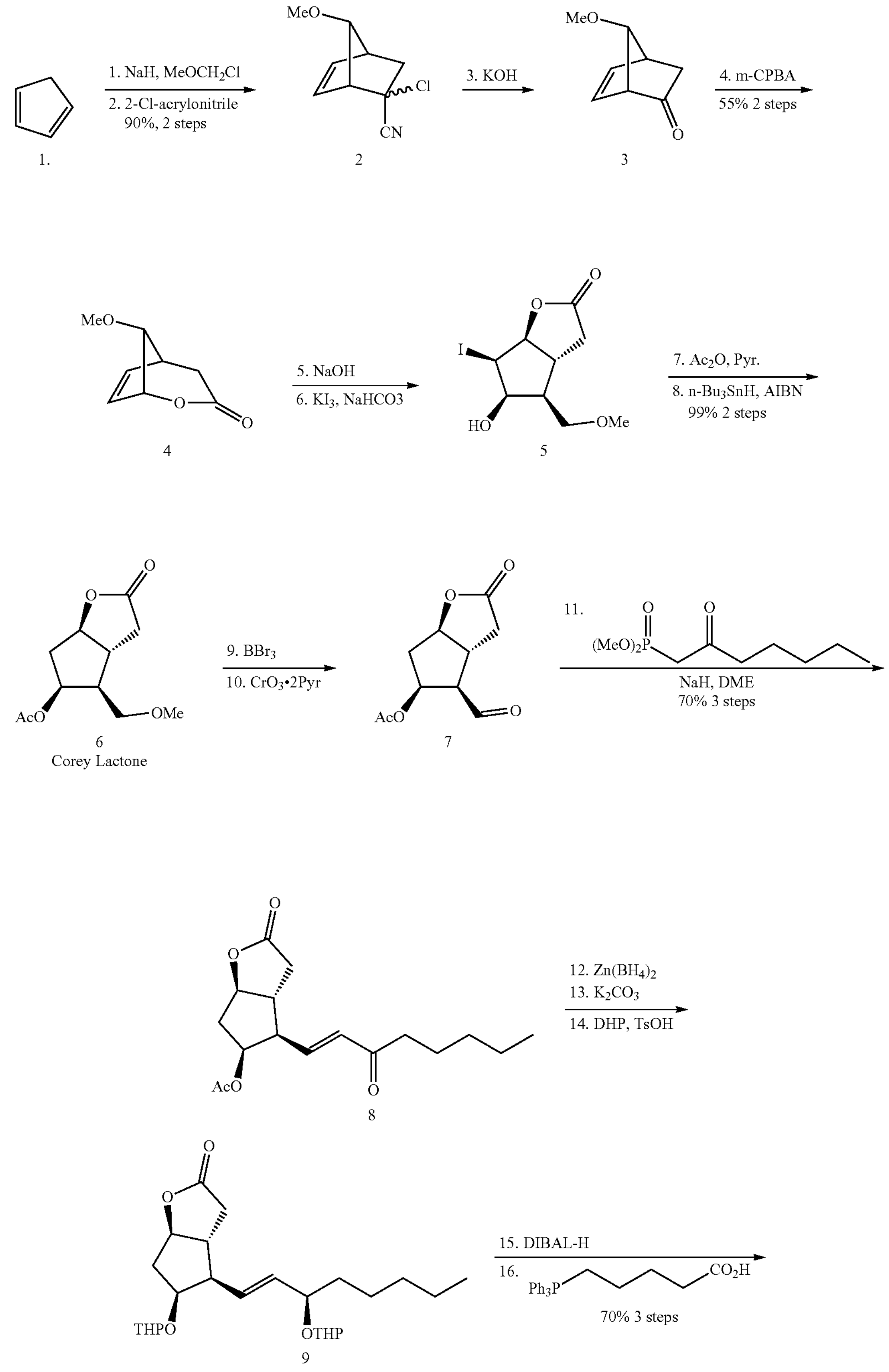

-continued
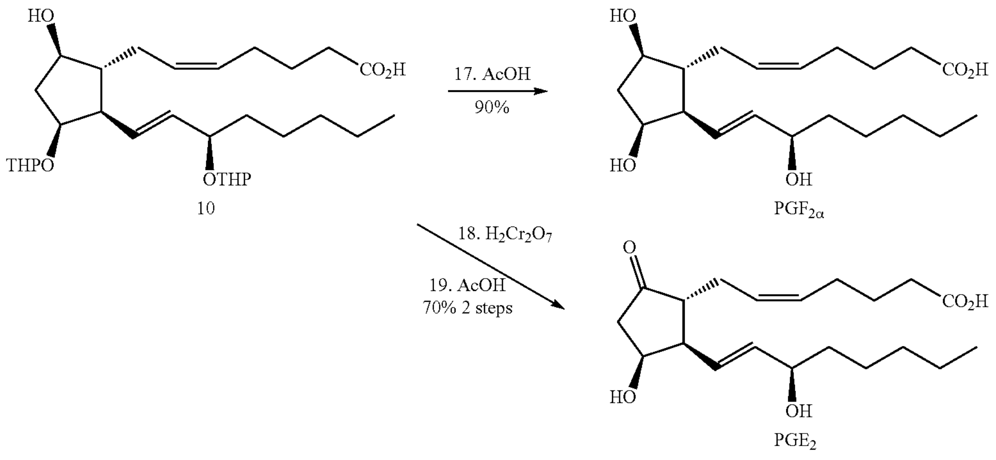
10
$PGF_{2\alpha}$
$PGE_2$
Scheme 2. Protaglandins' synthesis via Corey lactone
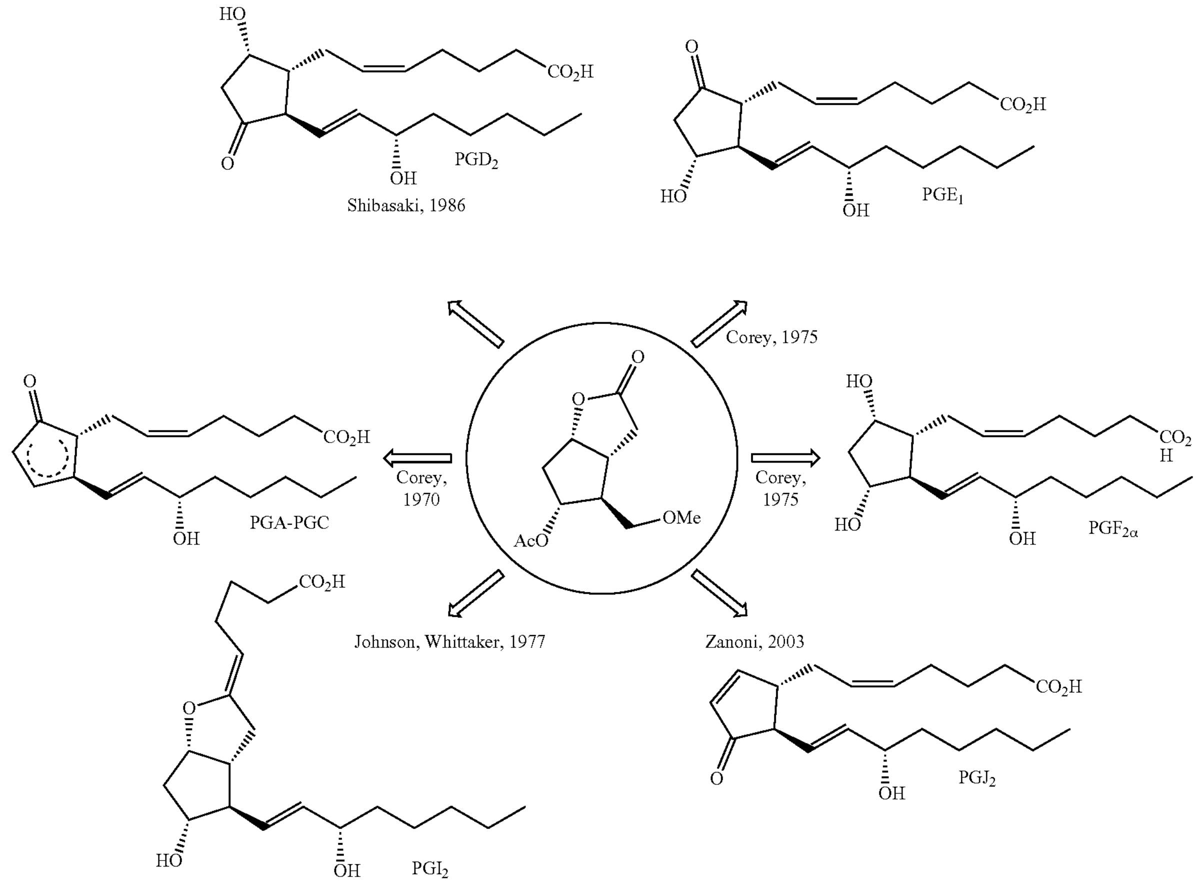
$PGD_2$
$PGE_1$
PGA-PGC
$PGF_{2\alpha}$
$PGI_2$
$PGJ_2$ Although many molecules of the prostaglandin family can be obtained from Corey lactone, a key intermediate in the Corey's route through subsequent conversion, the synthesis procedure of this intermediate is complicated, which include nine steps of reactions starting from cyclopentadiene, and the subsequent conversion from the intermediate to the final product also requires nearly ten steps or even more than ten steps of reactions.

Scheme 3. Aggarwal's route

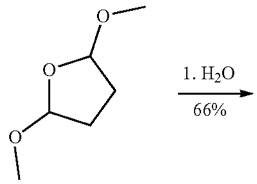

11

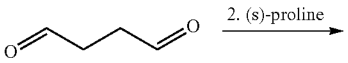

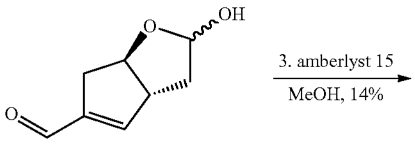

12

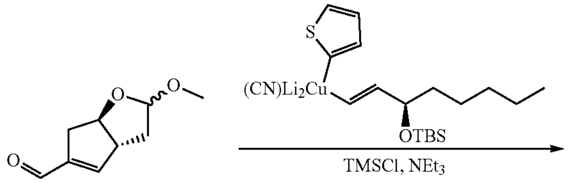

13

-continued

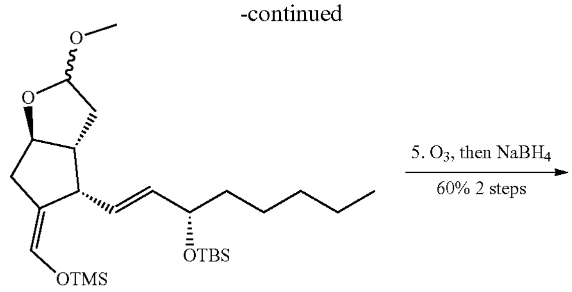

14

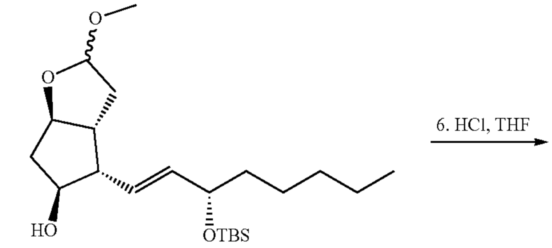

15

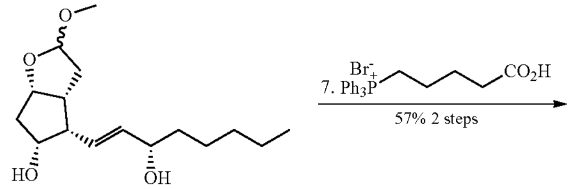

16

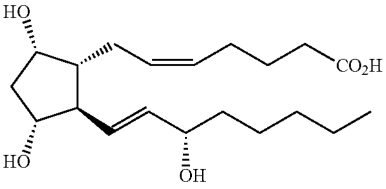
$PGF_{2\alpha}$

The synthesis procedure of Aggarwal's route is simple. However, the yield of the first-step reaction is very low, and only 14%, causing it difficult to be scaled up for use. The conversion of the key intermediate to the final product is also difficult, and the chemical selectivity of the reaction is poor, with a low yield.

Scheme 4. Shi's route

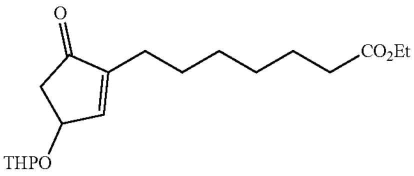
21

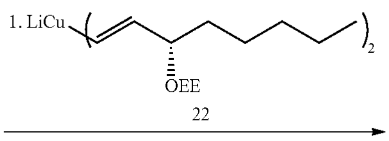

22

-continued
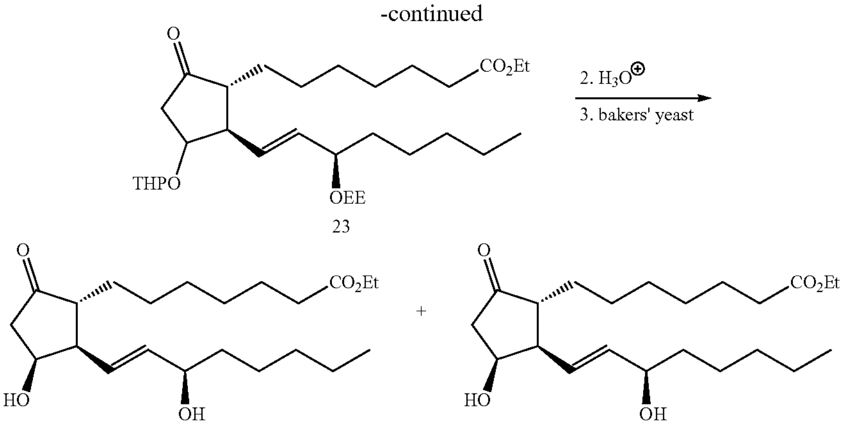
23
24 + 25
The Shi's route refers to a racemic reaction, and a further resolution is required to obtain the prostaglandin compound.
Scheme 5. Stork's route
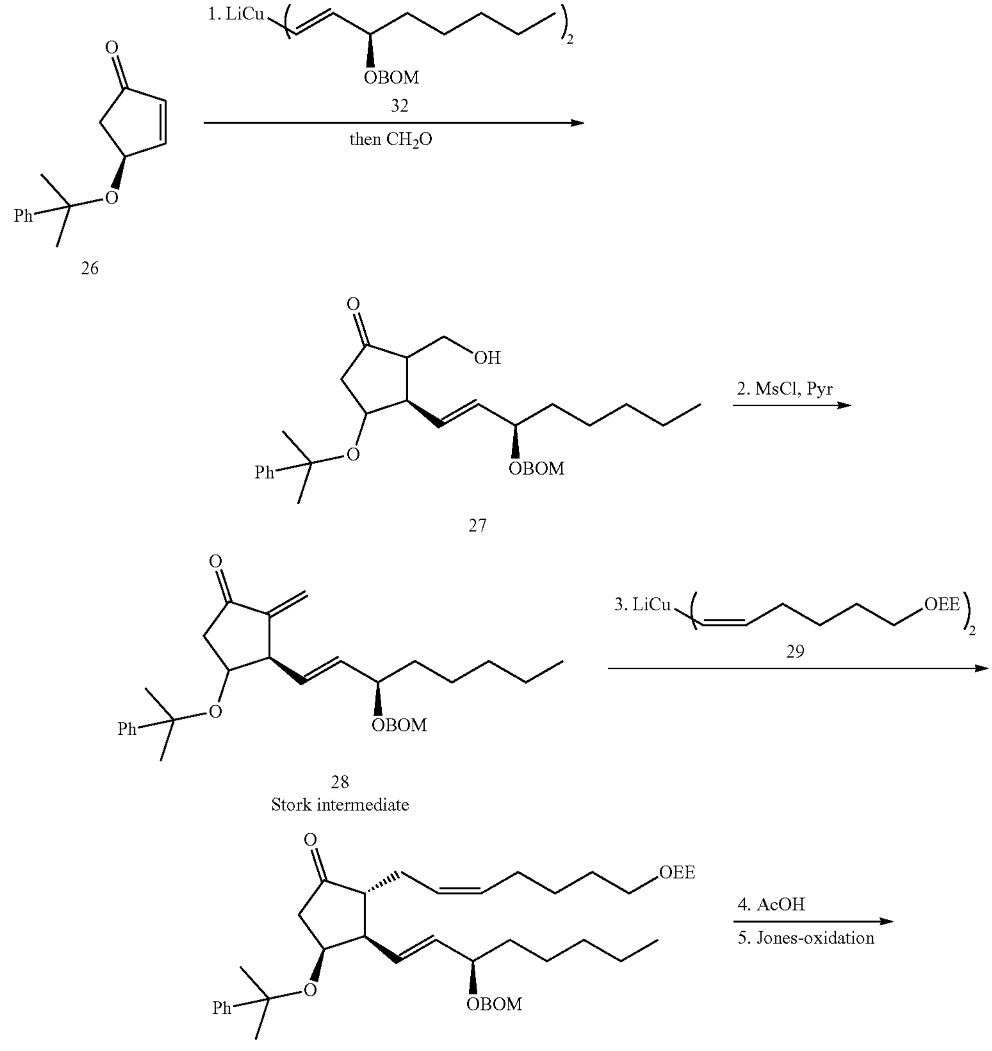
26
27
28
Stork intermediate
30

-continued

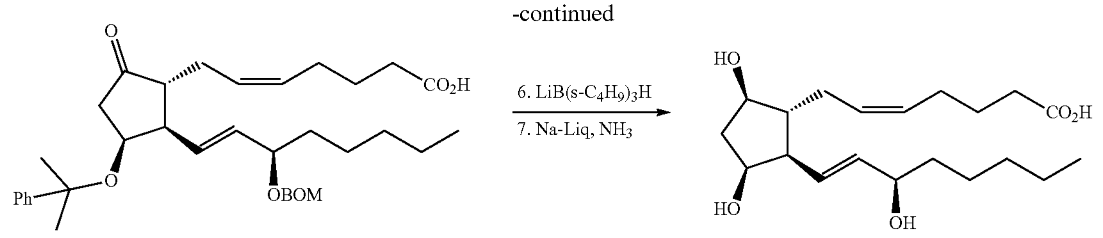

31 $PGF_{2\alpha}$

The Stork's route involves a key intermediate cyclopentenone. The synthesis of this intermediate is difficult, and generally realized by an enzymatic resolution reaction, which is adverse to atomic economy. Moreover, the conversion steps from this intermediate to the final product are troublesome, in which an organocopper lithium reagent that is sensitive to water and air is used, causing difficulty in operation.

Scheme 6. Noyori's route

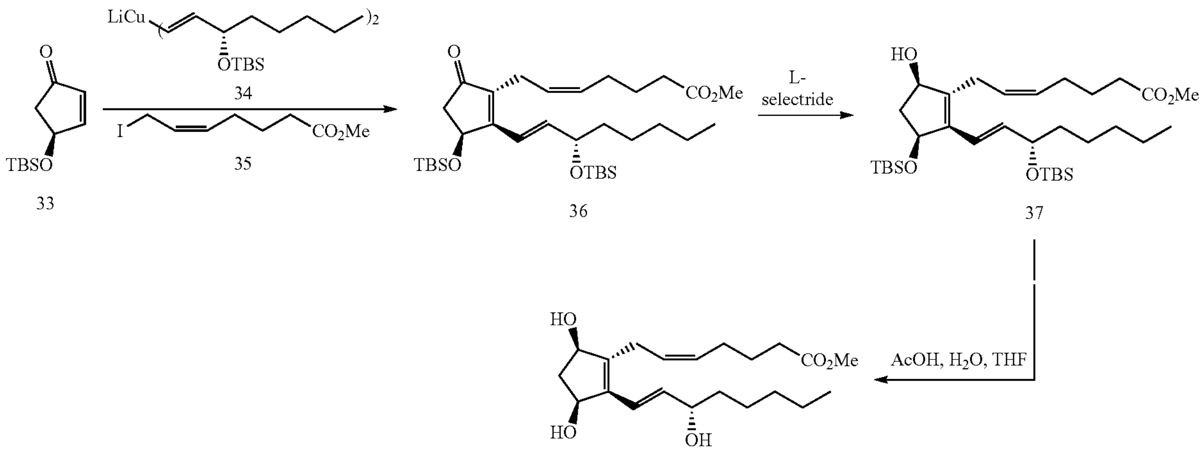

33 34 35 36 37 37-a

The Noyori's route also involves the difficult-to-be-synthesized cyclopentenone intermediate, and the organocopper lithium reagent that is sensitive to water and air, as well as a highly toxic organotin reagent, causing great harm to the humans and environment.

When used for the synthesis of prostaglandin compounds, the aforementioned procedures are complex, and the yield and product purity need to be further improved.

The present invention aims to provide a key intermediate for the synthesis of a prostaglandin compound and a preparation method thereof, for use in the synthesis of a prostaglandin. The present invention has the advantages of simple reaction operation, good functional group tolerance, no highly toxic chemicals involved in the synthetic route, being green and environmentally friendly, high yield and purity of the product, and more conducive to industrial application.

SUMMARY

In view of the problems existing in the prior art, the present invention provides a key intermediate for the synthesis of a prostaglandin compound and a preparation method thereof. Particularly, the present invention is accomplished through the following technical solutions.

A key intermediate for the synthesis of a prostaglandin compound has a structure shown below:

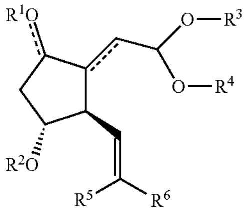

I or

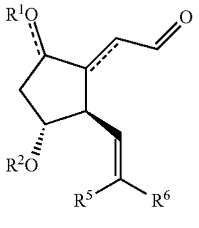

II or

-continued

III

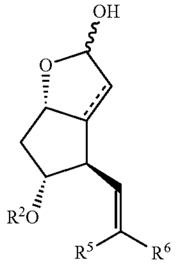

wherein ⎓ denotes a single bond or double bond, and if it is a double bond, $R^1$ is absent; and wherein $R^1$ and $R^2$ are each H or protecting groups; $R^3$ and $R^4$ are the same or different alkyl or aryl, or $R^3$ and $R^4$ form a ring; and $R^5$ and $R^6$ are the same or different H, alkyl, or aryl.

The alkyl refers to a linear or branched alkyl group, including, but not limited to, For example, a $C_{1-6}$ alkyl group or a $C_{3-7}$ monocyclic cycloalkyl group.

The $C_{1-6}$ alkyl group is selected from methyl, ethyl, n-propyl, isopropyl, n-butyl, isobutyl, s-butyl, t-butyl, n-pentyl, isopentyl, neopentyl, s-pentyl, t-pentyl, n-hexyl, isohexyl, neohexyl, s-hexyl, and t-hexyl.

The $C_{3-7}$ monocyclic cycloalkyl group is selected from cyclopropyl, cyclobutyl, cyclopentyl, cyclohexyl, and cycloheptyl.

The aryl refers to an aromatic ring structure containing a single ring or a fused polycyclic ring, including, but not limited to, naphthyl and the like. Further, the aryl group can be substituted with one or more halogens or alkyl groups.

$R^3$ and $R^4$ form a ring by connecting the carbon chains, wherein one or more carbon atoms in the carbon chains can be replaced by a heteroatom selected from O, N and S.

In a preferred embodiment of the present invention, the key intermediate for the synthesis of a prostaglandin compound has a structure shown below:

Ia

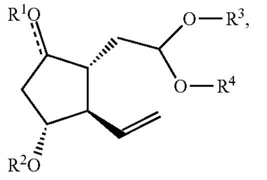

or

Ib

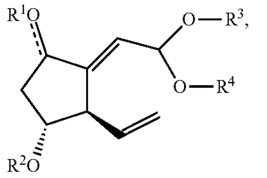

or

IIa

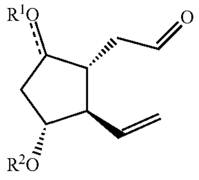

or

-continued

IIb

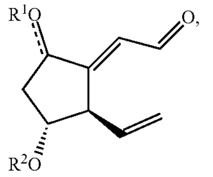

or

IIIa

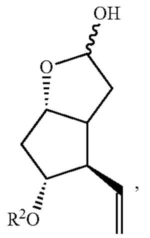

, or

IIIb

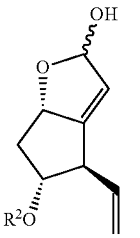

wherein $R^1$, $R^2$, $R^3$, and $R^4$ are as defined above.

In a preferred embodiment of the present invention, the key intermediate for the synthesis of a prostaglandin compound has a structure shown below:

1

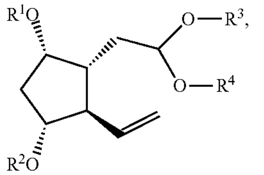

or

2

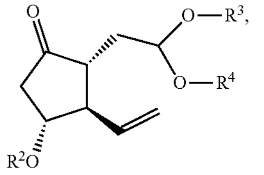

or

3

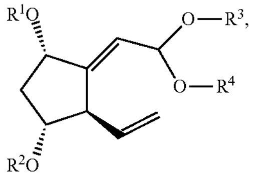

or

4

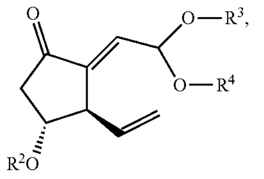

or

-continued

5

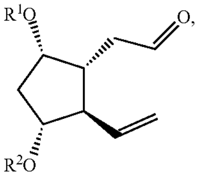

or

6

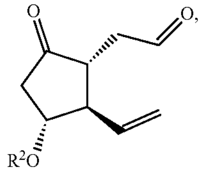

wherein $R^1$, $R^2$, $R^3$, and $R^4$ are as defined above.

In a preferred embodiment of the present invention, the key intermediate for the synthesis of a prostaglandin compound has a structure shown below:

7

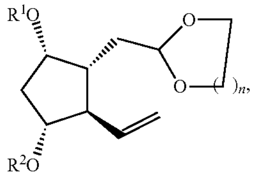

or

8

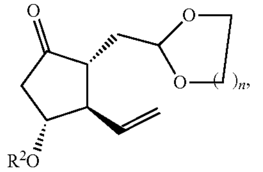

or

9

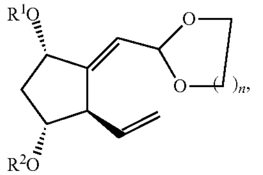

or

10

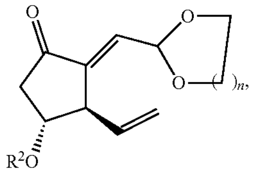

wherein $R^1$ and $R^2$ are as defined above, and n is an integer from 1 to 3.

In a preferred embodiment of the present invention, the key intermediate for the synthesis of a prostaglandin compound has a structure shown below:

11

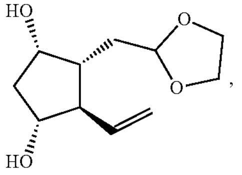

12

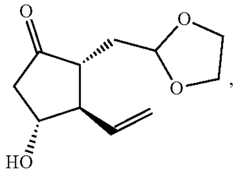

13

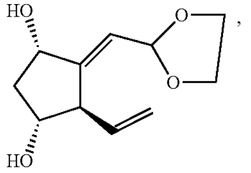

14

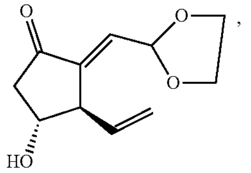

15

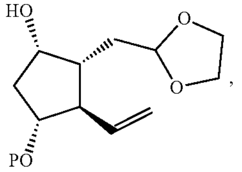

16

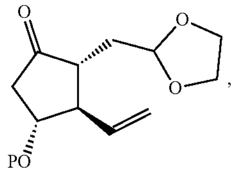

17

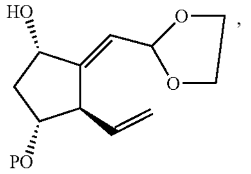

18

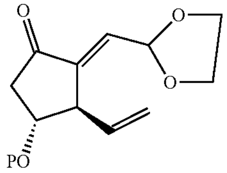

wherein P is a protecting group.

In a preferred embodiment of the present invention, the protecting group is selected from an ether protecting group, an acyl protecting group, a silyl ether protecting group, an acetal protecting group, or other common protecting groups in chemical synthesis.

The ether protecting group includes, for example, methyl or substituted methyl, preferably lower alkoxymethyl, particularly methoxymethyl (MOM), methylthiomethyl, p-nitrobenzyloxymethyl, guaiacylolmethyl, lower alkoxy-lower alkoxymethyl, particularly preferably 2-methoxyethoxymethyl (MEM), and 2, 2, 2-trifluoroethoxymethyl; tetrahydropyrans; 3-bromotetrahydropyrans; substituted ethyl, such as 1-ethoxyethyl, 1-(2-chloroethoxy)ethyl, 1-[2-(trimethylsilyl)ethoxy]ethyl; substituted phenyl ethers, such as p-chlorophenyl, P-methoxyphenyl, and p-nitrophenyl; and silyl ethers, such as trimethylsilyl, triethylsilyl, triisopropylsilyl, and dimethylisopropylsilyl, etc.

In a preferred embodiment of the present invention, the key intermediate for the synthesis of a prostaglandin compound has a structure shown below:

19

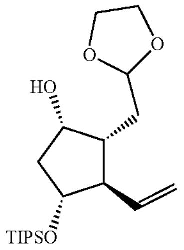

,

20

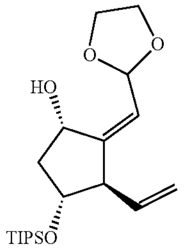

,

21

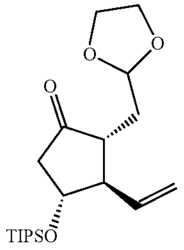

,

22

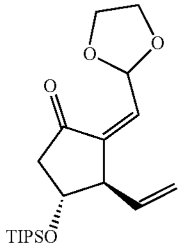

,

23

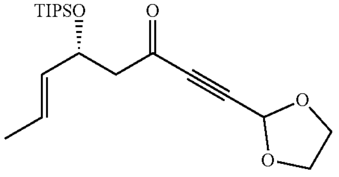

.

In a preferred embodiment of the present invention, a method for preparing the key intermediate comprises steps of:

a) asymmetrically reducing compound S1 to obtain chiral alcohol compound S2, and then protecting hydroxyl group of the chiral alcohol compound S2 with silane to obtain Weinreb amide compound S3;

b) subjecting the Weinreb amide compound S3 to an addition reaction with an alkyne reagent to obtain enyne compound S4;

c) subjecting the enyne compound S4 to a Zhang enyne cycloisomerization to obtain five-membered ring S5;

d) conjugating the five-membered ring S5 to reduce double bond thereof to obtain compound S6, and further reducing ketone of the compound S6 to obtain compound S7; and e) deprotecting the compound S7 by removing TIPS thereof to obtain compound S8; referring to the following reaction route:

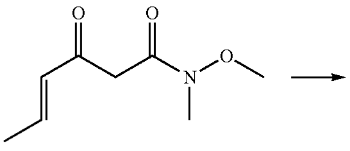

S1

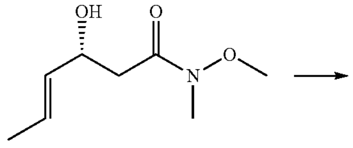

S2

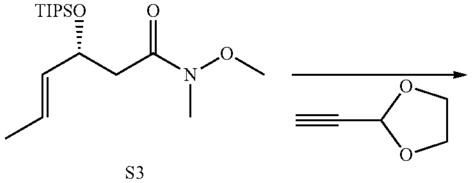

S3

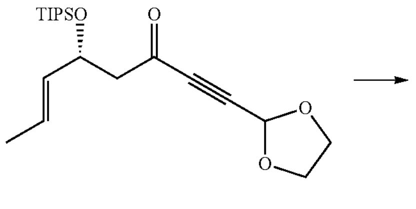

S4

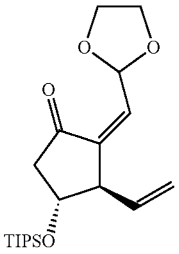

S5

-continued

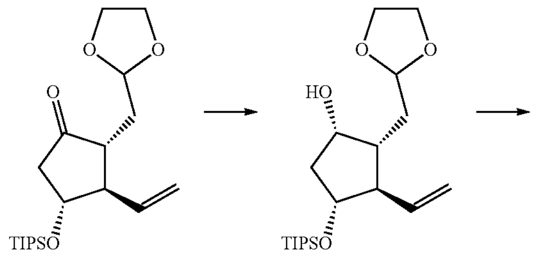

S6

S7

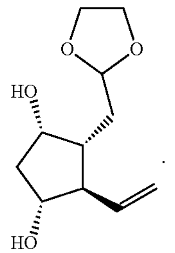

S8

Other intermediates described above can be synthesized based on this synthetic route by adaptively adjusting the groups.

In a preferred embodiment of the present invention, the preparation method is as follows:

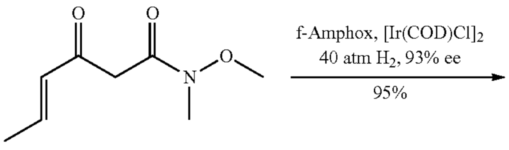

S1

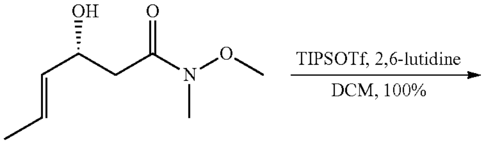

S2

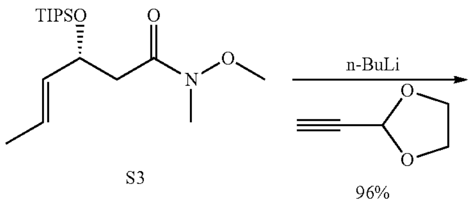

S3

96%

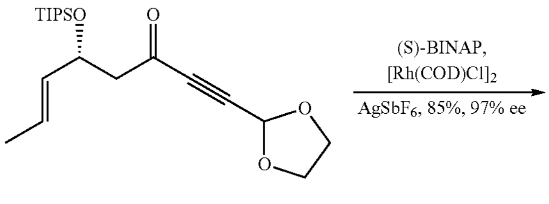

S4

-continued

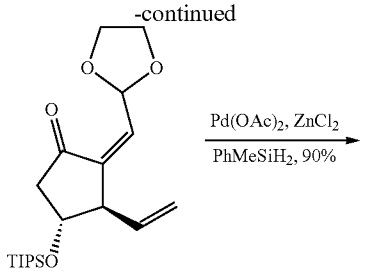

S5

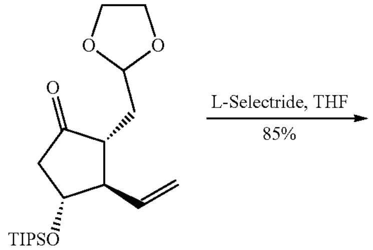

S6

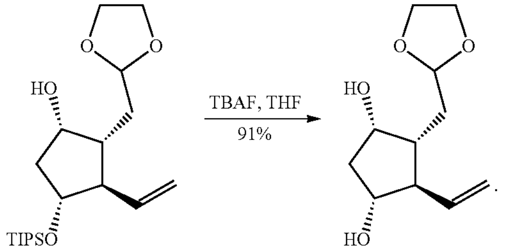

S7

S8

In a preferred embodiment of the present invention, the aforementioned key intermediate for the synthesis of a prostaglandin compound is used to prepare the prostaglandin compound.

In a preferred embodiment of the present invention, the aforementioned key intermediate for the synthesis of a prostaglandin compound is reacted with intermediates represented by the following formulas to prepare the prostaglandin compounds. The intermediate is selected from:

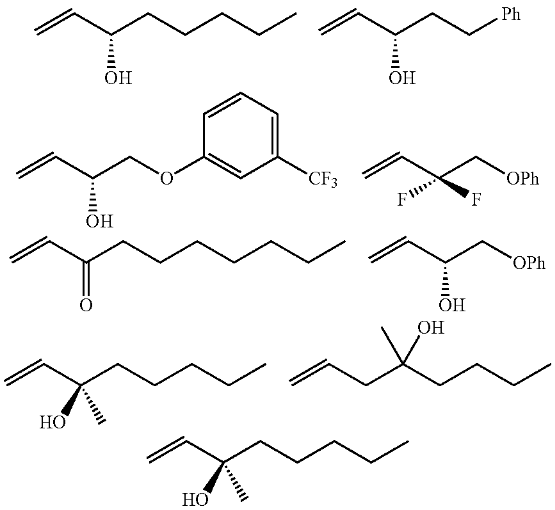

-continued

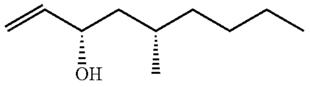

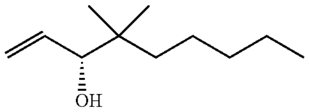

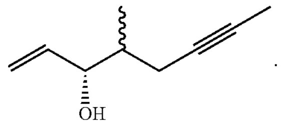

In a preferred embodiment of the present invention, the intermediate is prepared by the following preparation method, wherein R is the corresponding group in the aforementioned intermediate compound:

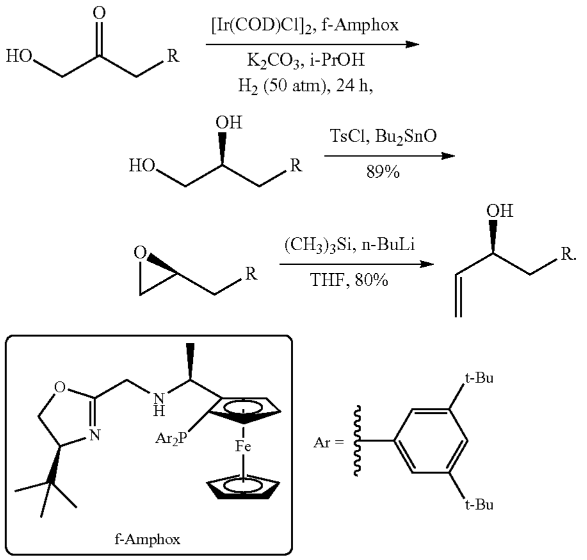

In a preferred embodiment of the present invention, the intermediate is prepared by the following preparation method:

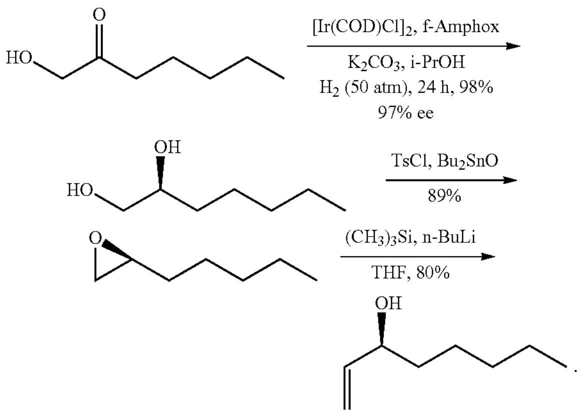

-continued

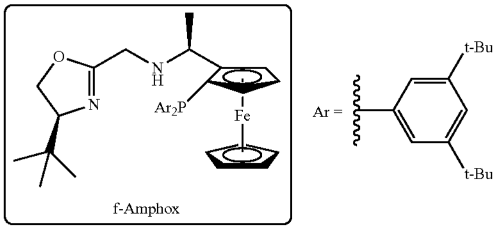

In a preferred embodiment of the present invention, the intermediate is prepared by the following preparation method:

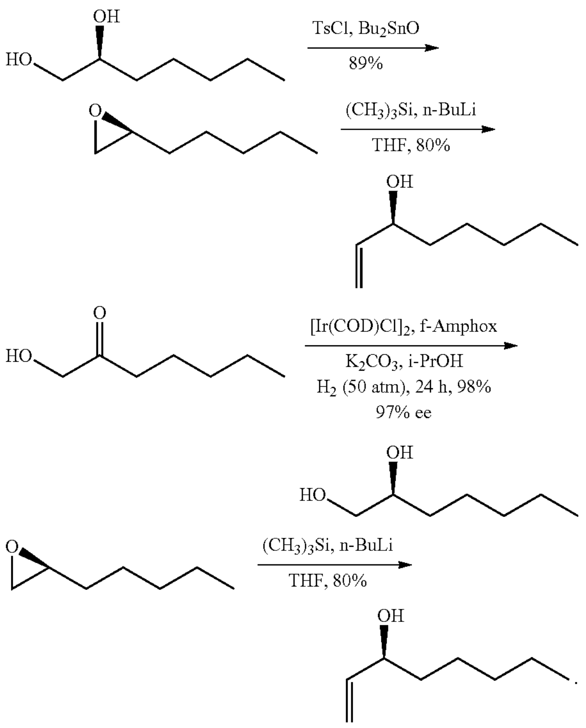

In a preferred embodiment of the present invention, the prostaglandin compound is selected from:

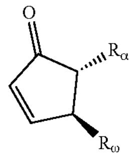

PGA

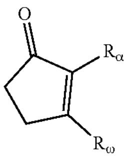

PGB

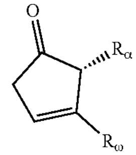
PGC
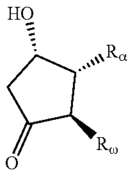
PGD
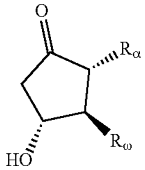
PGE
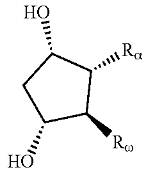
$PGF_a$
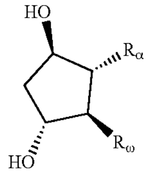
$PGF_\beta$
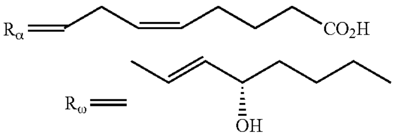
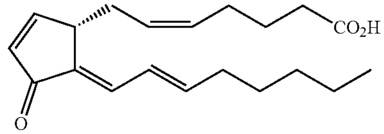
$PGJ_2$
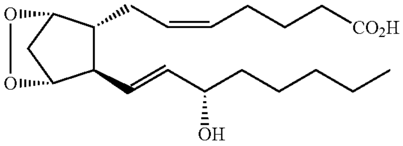
$PGH_2$
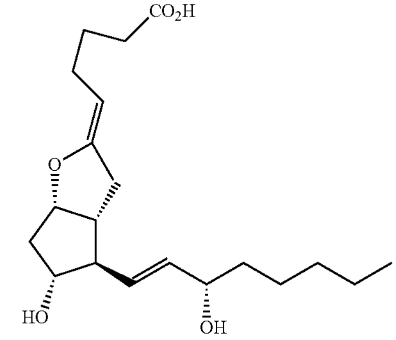
$PGI_2$
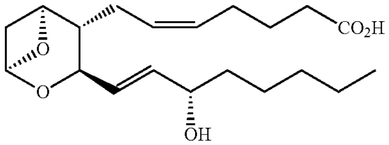
$TXA_2$
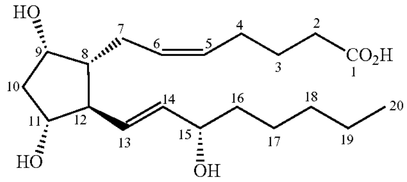
$PGF_{2\alpha}$
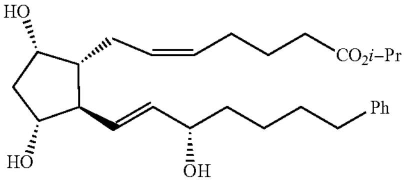
Latanoprost
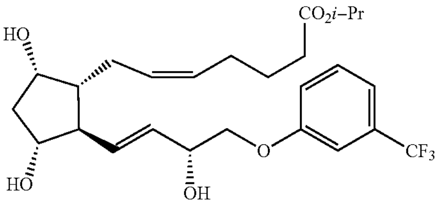
Trevoprost
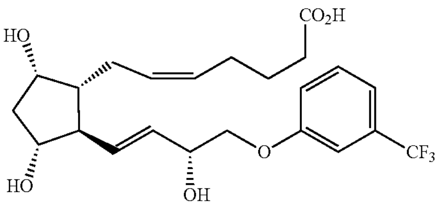
Fluprostenol
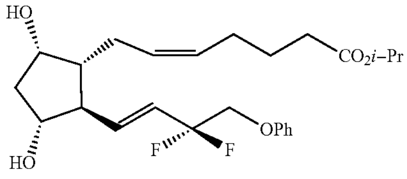
Tafluprost -continued
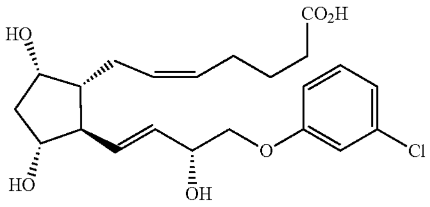
Cloprostenol
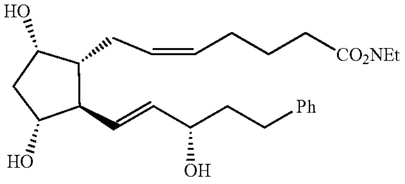
Blmatoprost
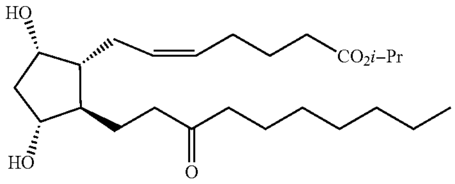
Unoprostone isopropyl ester
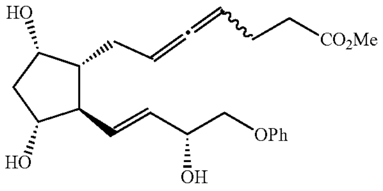
(±)-Fenprostaiene
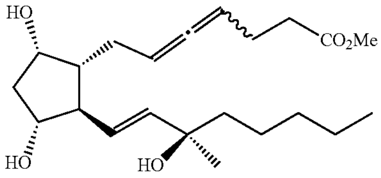
Prostalene
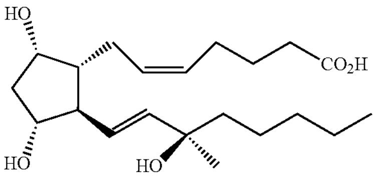
Carboprost
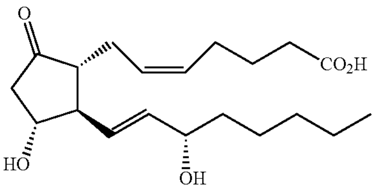
Dinoprostone
-continued
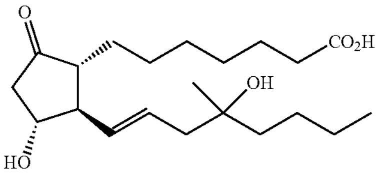
Misoprostol
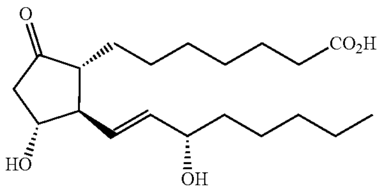
Alprostadl (PGE1)
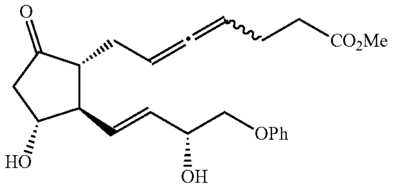
(±)Enprostil
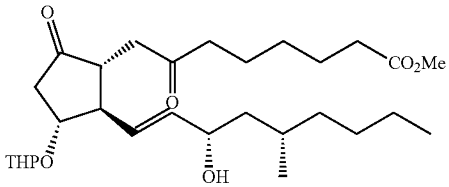
Omoprostol
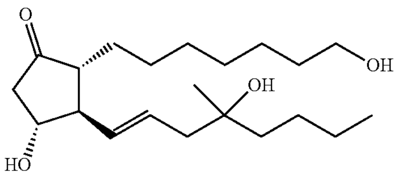
Rioprostol
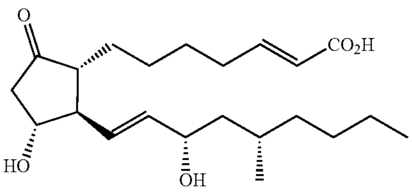
Limaprost
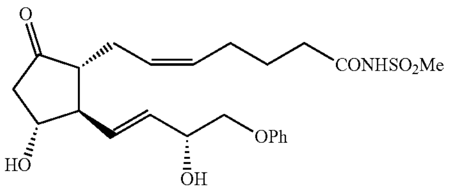
Sulprostone -continued

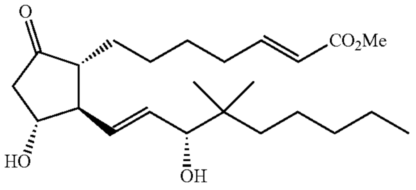

Gemeprost

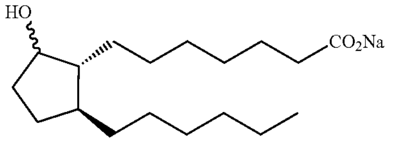

Rosaprostol

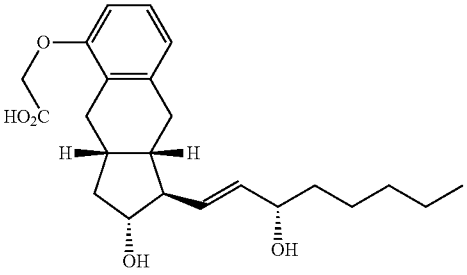

Treprostinil

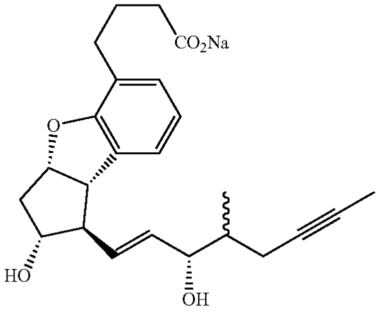

Beraprost

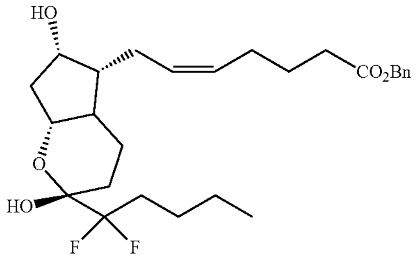

Lubiprostone

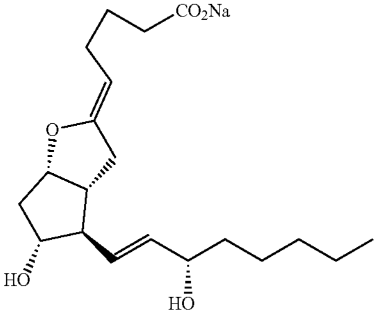

Epoprostenol

-continued

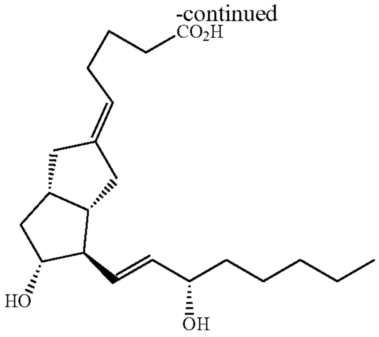

Carbacyclin

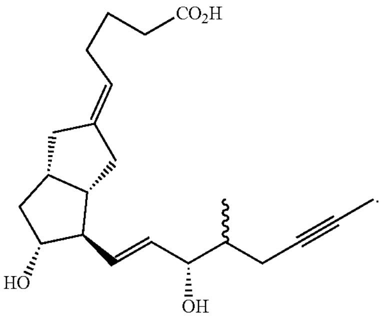

Iioprost

Beneficial Effects of the Present Invention Over the Prior Art

The present invention provides a key intermediate for the synthesis of a prostaglandin. When the key intermediate is used in the synthesis of the prostaglandin compound, the present invention has advantages of simplified process, highly environmentally tolerant functional groups of the intermediate, no highly toxic chemicals involved in the synthetic route, being green and environmentally friendly, improved yield and product purity, reduced production cost, and easy industrialization.

With respect to the synthetic route, the synthetic route provided by the present invention starts from different intermediates to prepare different prostaglandin compounds of different skeletal structures. Therefore, compared with other routes, it can be widely used in the synthesis of various prostaglandin compounds.

BRIEF DESCRIPTION OF THE DRAWINGS

FIG. 1 shows the structures of a specific intermediate according to the present application and prostaglandin compounds.

DESCRIPTION OF THE EMBODIMENTS

The present invention will be further described in detail below with reference to examples and accompanying drawings. However, the present invention is not limited thereto.

Example 1

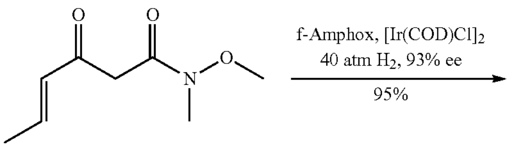

S1

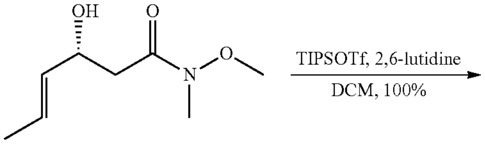

S2

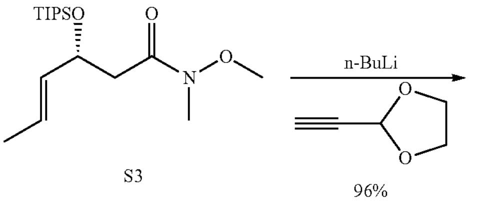

S3

96%

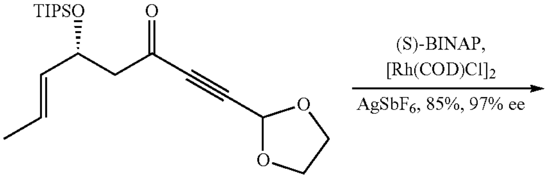

S4

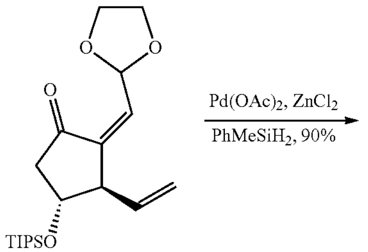

S5

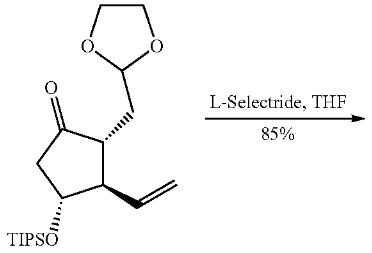

S6

-continued

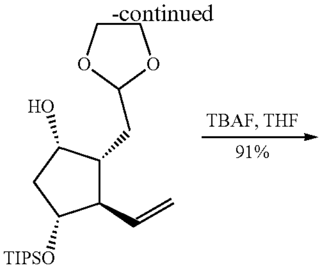

S7

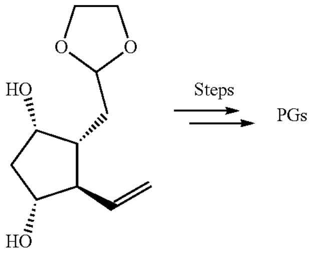

S8

Step 1:

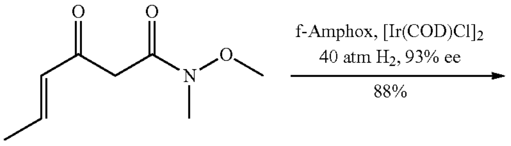

S1

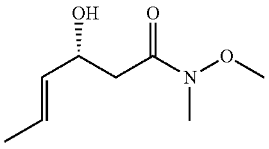

S2

Hydrogenation step of 1 mmol substrate (S/C=1000): In an argon-filled glove box, f-amphox (5.52 mg, 0.01 mmol) and a metal precursor $[Ir(COD)Cl]_2$ (3.35 mg, 0.05 mmol) were dissolved in anhydrous and anaerobic i-PrOH (1 mL), stirred at room temperature for 1 hr, to obtain a catalyst solution of 10 μmol/mL. In the glove box, Compound S1 (171 mg, 1 mmol) was dissolved in a 20 mL reaction flask containing 10 mL of anhydrous and anaerobic toluene, then MeOK (0.7 mg, 0.01 mmol) was added to the reaction system, and finally 0.1 mL of the fresh catalyst prepared above was added. The reaction flask was transferred to a hydrogenation reactor, and the reactor was purged three times with hydrogen and then introduced with 40 atm of hydrogen. The reaction system was stirred for 24 hrs at room temperature. After the reaction, hydrogen in the reactor was discharged, and the reaction solution was dried by rotary evaporation. The obtained crude product was subjected to silica gel column chromatography with eluent of petroleum ether:ethyl acetate=2:1, to obtain 150 mg of a liquid product S2 as a light yellow oil (yield 88%).

Step 2:

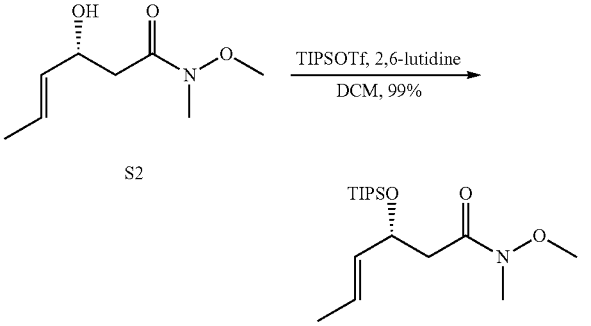

S2

S3

Compound S2 (1.73 g, 10 mmol) and 10 mL of dry DCM were added to a 25 mL reaction flask, and then 2, 6-lutidine (1.6 g, 15 mmol) was added to the reaction system. Finally, TIPSOTf (3.67 g, 12 mmol) was slowly added dropwise to the reaction solution, and reacted at room temperature for 30 minutes. The reaction was monitored by TLC. After the reaction was completed, water was added to stop the reaction. The reaction solution was extracted with DCM (20 mL*3), and the organic phases were combined with anhydrous sodium sulfate and dried with anhydrous sodium sulfate by rotary evaporation. The obtained crude product was subjected to silica gel column chromatography with eluent of petroleum ether:ethyl acetate=4:1, to obtain 3.28 g of a liquid product S3 as a light yellow oil (yield 99%).

Step 3:

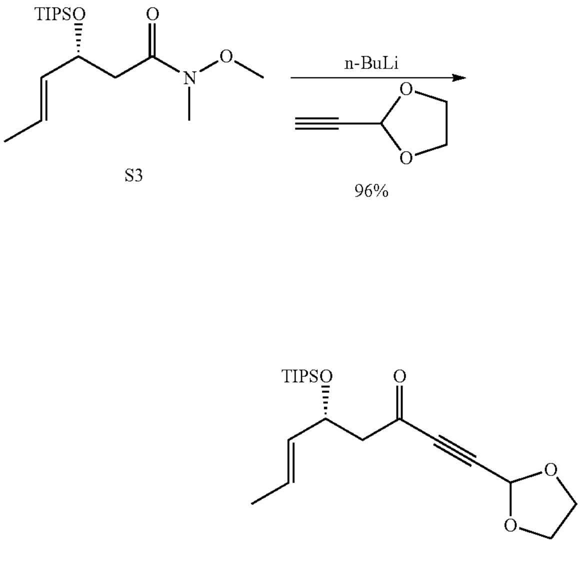

S3

S4

Under an argon atmosphere at −78° C., Compound S3 (294 mg, 3 mmol) and 5 mL of anhydrous THF were added to a 25 mL dry reaction flask, and then 1.25 mL (2.4 M, 3 mmol) of n-butyl lithium was added dropwise to the reaction solution, and reacted at −78° C. for 30 minutes. Then Compound (328 mg, 1 mmol) was dissolved in 2 mL of dry THF, and slowly added dropwise to the above reaction solution. The reaction solution was then immediately heated to −10° C., and continuously reacted for 30 minutes. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=20:1, to obtain 351 mg of a liquid product S4 as a light yellow oil (yield 96%).

$^1$H NMR (600 MHz, $CDCl_3$) δ 5.78 (s, 1H), 5.65-5.56 (m, 1H), 5.43 (dd, J=15.2, 7.3 Hz, 1H), 4.72 (dd, J=13.3, 6.5 Hz, 1H), 4.10-3.99 (m, 2H), 3.99-3.88 (m, 2H), 2.84 (dd, J=14.8, 6.6 Hz, 1H), 2.68 (dd, J=14.8, 6.3 Hz, 1H), 1.64 (d, J=6.3 Hz, 3H), 1.01 (s, 21H). $^{13}$C NMR (151 MHz, $CDCl_3$) δ 184.67 (s), 133.21 (s), 126.61 (s), 92.51 (s), 85.37 (s), 82.66 (s), 70.22 (s), 64.56 (s), 54.40 (s), 17.96 (s), 17.90 (s), 17.60 (s), 17.34 (s), 12.26 (s).

Step 4:

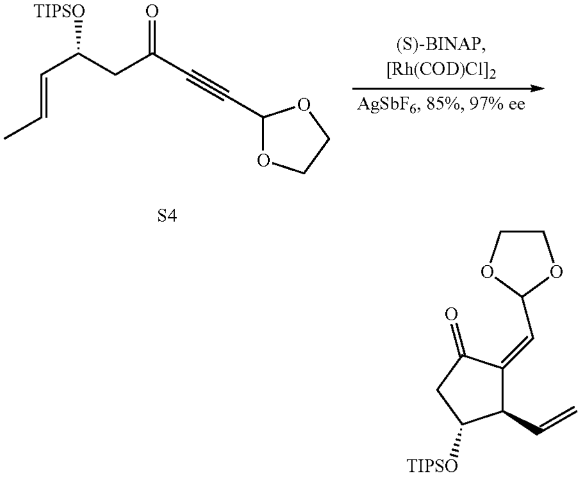

S4

S5

In an argon-filled glove box, Compound S4 (3.28 g, 9 mmol) was dissolved in a 100 mL reaction flask containing 50 mL of anhydrous and anaerobic DCE. (S)-BINAP (0.558 g, 0.9 mmol) and $[Rh(COD)Cl]_2$ (0.22 g, 0.45 mmol) were added to the reaction flask and stirred at room temperature for 5 minutes. Finally, $AgSbF_6$ (0.614 g, 1.8 mmol) was added and continuously reacted at room temperature for 10 minutes. The reaction was monitored by TLC. After the reaction was completed, the reaction solution was dried by rotary evaporation. The obtained crude product was subjected to silica gel column chromatography with eluent of petroleum ether:ethyl acetate=12:1, to obtain 2.78 g of a liquid product S5 as a light yellow oil (yield 85%).

$^1$H NMR (600 MHz, $CDCl_3$) δ 6.33 (d, J=7.4 Hz, 1H), 5.73-5.69 (m, 1H), 5.69-5.64 (m, 1H), 5.24 (dd, J=29.5, 13.6 Hz, 2H), 4.24 (q, J=6.7 Hz, 1H), 4.05-3.97 (m, 2H), 3.96-3.90 (m, 2H), 3.31 (t, J=6.0 Hz, 11H), 2.72 (dd, J=17.9, 6.4 Hz, 11H), 2.40 (dd, J=17.9, 7.2 Hz, 1H), 1.03 (s, 21H). $^{13}$C NMR (151 MHz, $CDCl_3$) δ 203.43 (s), 142.37 (s), 136.27 (s), 135.06 (s), 119.54 (s), 96.84 (s), 72.37 (s), 65.20 (d, J=5.6 Hz), 57.37 (s), 48.52 (s), 17.93 (s), 17.90 (s), 12.13 (s).

Step 5:

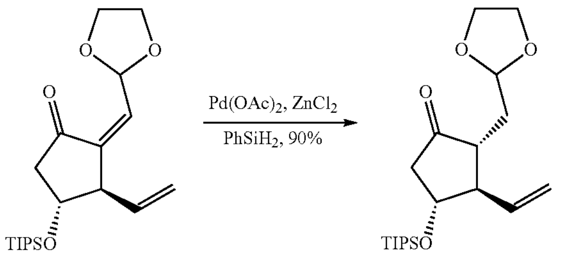

S5 S6

Under an argon atmosphere, Compound S5 (366 mg, 1 mmol), anhydrous $ZnCl_2$ (204 mg, 1.5 mmol), $(Ph_3P)_4Pd$ (23.1 mg, 0.02 mmol) and 5 mL anhydrous THF were sequentially added to a 10 mL dry reaction flask. Then $Ph_2SiH_2$ (312 mg, 1.7 mmol) was added dropwise into the reaction flask, and reacted at 50° C. for 1 hr. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=20:1, to obtain 329 mg of a liquid product S6 as a light yellow oil (yield 90%).

$^1H$ NMR (600 MHz, $CDCl_3$) δ 5.84-5.73 (m, 1H), 5.19 (dd, J=21.0, 13.7 Hz, 2H), 5.13 (t, J=5.2 Hz, 1H), 4.22 (q, J=7.2 Hz, 1H), 3.98-3.89 (m, 2H), 3.88-3.79 (m, 2H), 2.69 (dd, J=18.1, 6.8 Hz, 1H), 2.61 (dd, J=18.1, 7.9 Hz, 1H), 2.25 (ddd, J=16.7, 14.7, 6.9 Hz, 2H), 2.06-1.98 (m, 1H), 1.82 (dt, J=12.1, 5.8 Hz, 1H), 1.04 (s, 21H). $^{13}C$ NMR (151 MHz, $CDCl_3$) δ 215.26 (s), 138.07 (s), 117.66 (s), 102.42 (s), 73.18 (s), 64.80 (s), 64.63 (s), 55.82 (s), 49.36 (s), 47.37 (s), 32.55 (s), 17.95 (d, J=5.5 Hz), 12.16 (s).

Step 6:

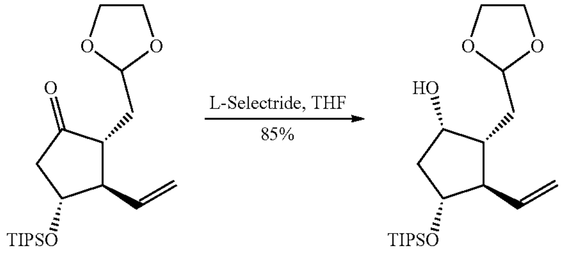

S6 S7

Under an argon atmosphere at −78° C., Compound S6 (368 mg, 1 mmol) and 5 mL of anhydrous THF were added to a 25 mL dry reaction flask, and then 1.2 mL (1 M, 1.2 mmol) of L-Selectride was added dropwise into the reaction solution, and reacted at −78° C. for 30 minutes. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=8:1, to obtain 312 mg of a liquid product S7 as a light yellow oil (yield 85%).

$^1H$ NMR (400 MHz, $CDCl_3$) δ 5.60 (dt, J=17.1, 9.6 Hz, 1H), 5.19-4.96 (m, 2H), 4.93 (t, J=4.5 Hz, 1H), 4.17 (td, J=7.2, 2.1 Hz, 1H), 4.06 (dd, J=11.2, 4.9 Hz, 1H), 4.03-3.92 (m, 2H), 3.90-3.79 (m, 2H), 3.04 (d, J=6.4 Hz, 1H), 2.33 (td, J=9.6, 5.2 Hz, 1H), 2.16 (dt, J=13.9, 6.1 Hz, 1H), 2.08-1.92 (m, 1H), 1.82 (dt, J=14.2, 4.0 Hz, 2H), 1.75-1.68 (m, 1H), 1.04 (s, 21H). $^{13}C$ NMR (101 MHz, $CDCl_3$) δ 139.57 (s), 116.20 (s), 103.90 (s), 78.41 (s), 72.73 (s), 64.97 (s), 64.63 (s), 57.64 (s), 44.94 (s), 43.13 (s), 31.64 (s), 17.97 (s), 12.05 (s).

Step 7:

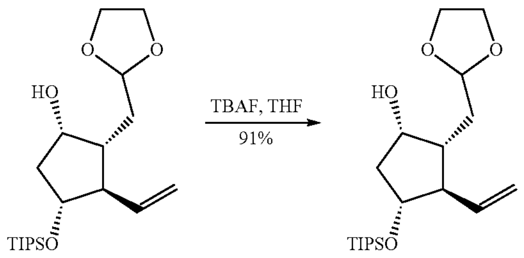

S7 S8

Compound S7 (370 mg, 1 mmol) and 5 mL of anhydrous THF were added to a 25 mL dry reaction flask, and then 1.5 mL (1 M in THF, 1.5 mmol) of TBAF was added dropwise to the reaction solution, and reacted at room temperature for 30 minutes. The reaction was monitored by TLC. After the reaction was completed, the reaction solution was extracted with $Et_2O$ (5 mL*3), and the organic phases were combined, and dried with anhydrous sodium sulfate by rotary evaporation. The obtained crude product was subjected to silica gel column chromatography with eluent of petroleum ether: ethyl acetate=2:1, to obtain 337 mg of a liquid product S8 as a light yellow oil (yield 91%).

$^1H$ NMR (400 MHz, $CDCl_3$) δ 5.62 (ddd, J=17.1, 10.1, 8.9 Hz, 1H), 5.16-5.01 (m, 2H), 4.89 (dd, J=5.1, 3.0 Hz, 1H), 4.22 (d, J=4.9 Hz, 1H), 4.05-3.93 (m, 2H), 3.92-3.81 (m, 3H), 3.10 (s, 1H), 2.54 (s, 1H), 2.34-2.20 (m, 2H), 1.96-1.82 (m, 2H), 1.79-1.67 (m, 2H). $^{13}C$ NMR (101 MHz, $CDCl_3$) δ 139.06 (s), 116.58 (s), 103.79 (s), 77.27 (s), 72.33 (s), 65.14 (s), 64.58 (s), 57.59 (s), 44.91 (s), 41.82 (s), 31.15 (s).

Example 2

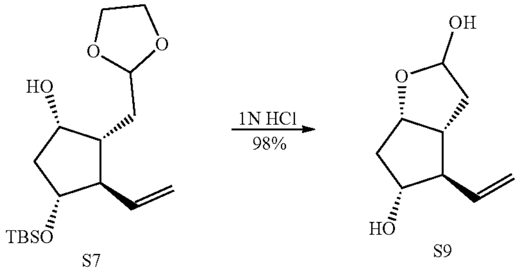

S7 S9

At room temperature, Compound S7 (2 g, 5.4 mmol) and 25 mL of THF were added to a 100 mL reaction flask, and then 25 mL of 1N HCl was added dropwise to the reaction solution and reacted at room temperature for 2 hrs. The reaction was monitored by TLC. After the reaction was completed, the reaction was terminated by adding a saturated sodium bicarbonate aqueous solution. The reaction solution was extracted with ethyl acetate (25 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 900 mg of a liquid product S9 as a light yellow oil (yield 98%).

$^1H$ NMR (400 MHz, $CDCl_3$) δ 5.62 (m, 1H), 5.14-5.04 (m, 2H), 4.89 (dd, J=5.1, 3.0 Hz, 1H), 4.22 (t, J=5.1 Hz, 1H), 4.05-3.93 (m, 2H), 3.91-3.80 (m, 3H), 3.10 (br, 1H), 2.54 (br, 1H), 2.33-2.20 (m, 2H), 1.95-1.81 (m, 2H), 1.79-1.68 (m, 2H). $^{13}C$ NMR (101 MHz, $CDCl_3$) δ 139.1, 116.6, 103.8, 77.3, 72.3, 65.1, 64.6, 57.6, 44.9, 41.8, 31.1. HRMS (ESI) Calcd for $C_{11}H_{18}O_4Na$ $[M+Na]^+$: 237.1097, found: 237.1095.

Example 3

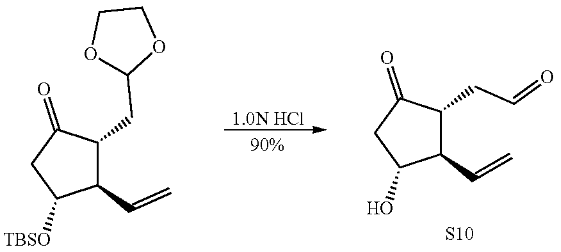

S6

S10

At room temperature, Compound S6 (1.5 g, 4.1 mmol) and 25 mL of THF were added to a 100 mL reaction flask, and then 25 mL of 1N HCl was added dropwise to the reaction solution and reacted at room temperature for 2 hrs. The reaction was monitored by TLC. After the reaction was completed, the reaction was terminated by adding a saturated sodium bicarbonate aqueous solution. The reaction solution was extracted with ethyl acetate (25 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 620 mg of a liquid product S10 as a light yellow oil (yield 90%).

$^1H$ NMR (600 MHz, $CDCl_3$) δ 9.73 (s, 1H), 5.76-5.70 (m, 1H), 5.25 (s, 1H), 5.22 (d, J=7.9 Hz, 1H), 4.18 (q, J=8.2 Hz, 1H), 2.84-2.77 (m, 2H), 2.70 (dd, J=18.7, 5.0 Hz, 1H), 2.56-2.45 (m, 2H), 2.41 (dd, J=18.6, 9.4 Hz, 1H), 2.25 (br, 1H). $^{13}C$ NMR (151 MHz, $CDCl_3$) δ 212.5, 199.3, 136.8, 119.4, 72.0, 55.3, 49.0, 45.2, 41.2. HRMS (ESI) Calcd for $C_9H1_2O_3Na$ $[M+Na]^+$: 191.0679, found: 191.0679.

Example 4

The key intermediate for the synthesis of a prostaglandin compound was reacted with an intermediate represented by the following formulas to prepare the prostaglandin compounds.

The structures of the intermediate is selected from:

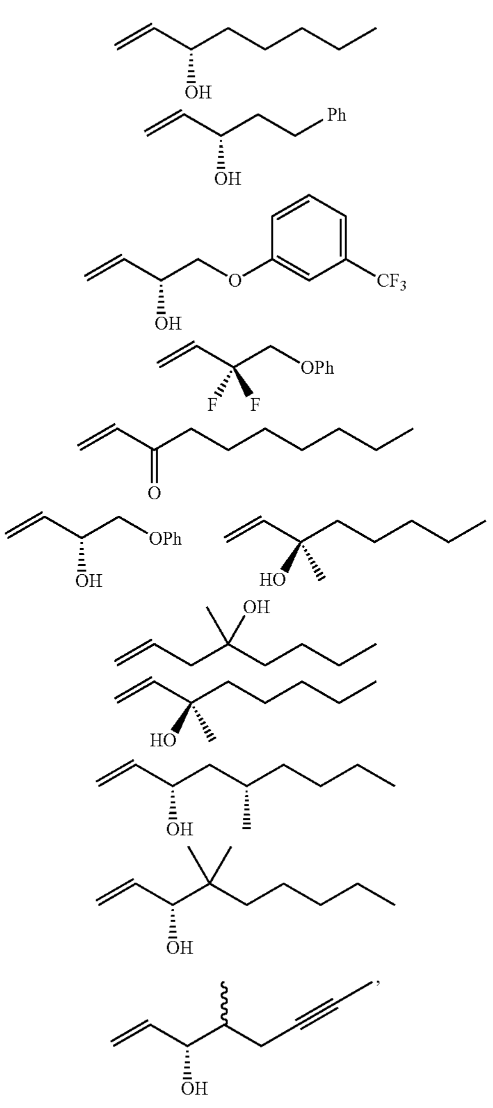

The preparation route was as follows:

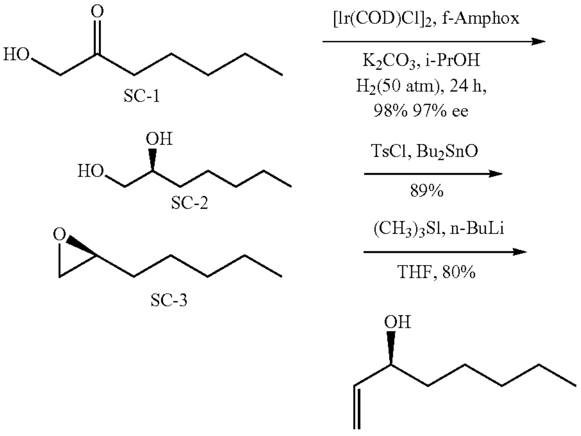

SC-1

SC-2

SC-3

SC-4

-continued

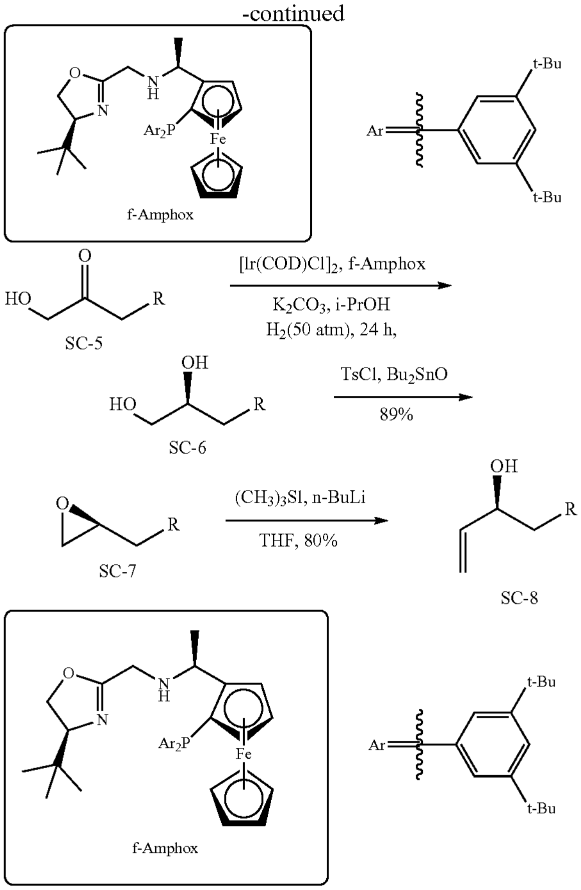

SC-5
SC-6
SC-7
SC-8

Example 5

The preparation method of a specific intermediate in Example 4 was as follows:

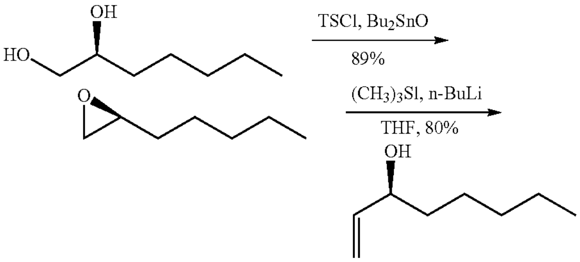

Step 1:

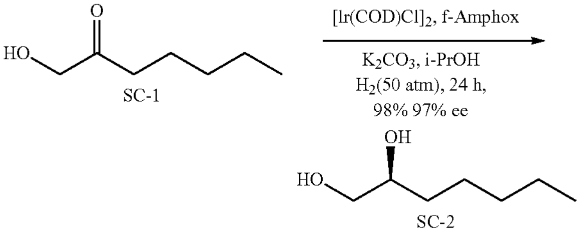

SC-1
SC-2

Hydrogenation step (S/C=1000): In an argon-filled glove box, f-amphox (55.2 mg, 0.1 mmol) and a metal precursor [Ir(COD)Cl]$_2$ (33.5 mg, 0.5 mmol) were dissolved in anhydrous and anaerobic i-PrOH (1 mL), stirred at room temperature for 1 hr, to obtain a catalyst solution of 100 μmol/mL. In the glove box, Compound SC-1 (2.6 g, 20 mmol) was dissolved in a 100 mL reaction flask containing 50 mL of anhydrous and anaerobic isopropanol, then K$_2$CO$_3$ (27.8 mg, 0.01 mmol) was added to the reaction system, and finally 0.2 mL of the fresh catalyst prepared above was added. The reaction flask was transferred to a hydrogenation reactor, and the reactor was purged three times with hydrogen and then introduced with 80 atm of hydrogen. The reaction system was stirred 24 hrs at room temperature. After the reaction, hydrogen in the reactor was discharged, and the reaction solution was dried by rotary evaporation. The obtained crude product was subjected to silica gel column chromatography with eluent of petroleum ether: ethyl acetate=2:1, to obtain 2.55 g of a liquid product SC-2 as a light yellow oil (yield 98%).

$^1$H NMR (400 MHz, CDCl$_3$) δ 3.66 (ddd, J=13.9, 9.2, 3.7 Hz, 2H), 3.42 (dd, J=11.0, 7.7 Hz, 1H), 2.49 (s, 2H), 1.47-1.38 (m, 3H), 1.31 (t, J=10.5 Hz, 5H), 0.88 (t, J=6.7 Hz, 3H). $^{13}$C NMR (101 MHz, CDCl$_3$) δ 72.29 (s), 66.60 (s), 32.93 (s), 31.79 (s), 25.24 (s), 22.49 (s), 13.91 (s).

Step 2:

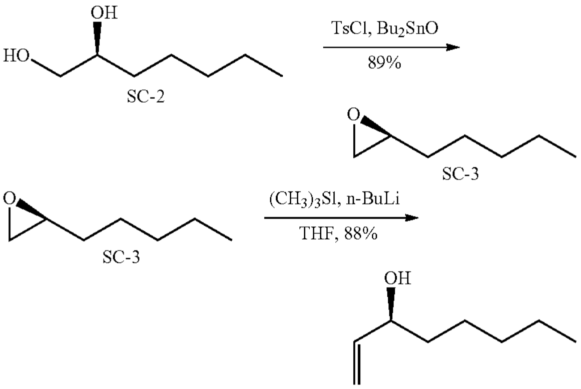

SC-2
SC-3
SC-3
SC-4

Under an argon atmosphere at −20° C., (Me)$_3$SI (26.8 g, 131.5 mmol) and 100 mL of anhydrous THF were added to a 250 mL dry reaction flask, and then 54 mL (2.4 M, 131.5 mmol) of n-butyl lithium was added dropwise to the reaction solution, and reacted at −20° C. for 30 minutes. Compound SC-3 (3.0, 26.3 mmol) was dissolved in 10 mL of dry THF, and slowly added dropwise to the above reaction solution. The reaction solution was then slowly heated to room temperature, and continuously reacted for 5 hrs. The reaction was monitored by TLC. After the reaction was completed, the reaction was terminated by adding a saturated ammonium chloride aqueous solution. The reaction solution was extracted with ethyl acetate (100 mL*3), and the organic phases were combined, and dried with anhydrous sodium sulfate by rotary evaporation. The obtained crude product was subjected to silica gel column chromatography with eluent of petroleum ether:ethyl acetate=20:1, to obtain 2.8 g of a liquid product SC-4 as a light yellow oil (yield 88%).

$^1$H NMR (400 MHz, CDCl$_3$) δ 5.94-5.79 (m, 1H), 5.15 (ddt, J=43.7, 10.4, 1.4 Hz, 2H), 4.13-4.06 (m, 1H), 1.58-1.48 (m, 3H), 1.35-1.28 (m, 5H), 0.88 (t, J=6.8 Hz, 3H). $^{13}$C NMR (101 MHz, $CDCl_3$) δ 141.30 (s), 114.46 (s), 73.23 (s), 36.95 (s), 31.71 (s), 24.97 (s), 22.56 (s), 13.98 (s).

Example 6

The preparation method of another specific intermediate in Example 4 was as follows:
Step 1:

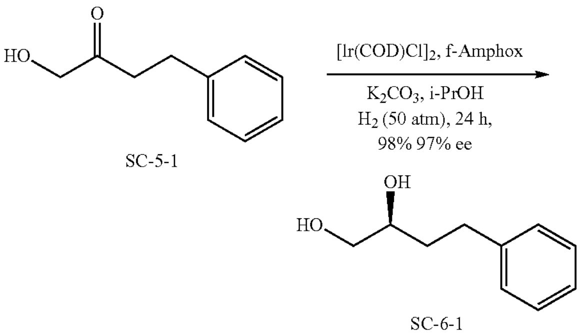

SC-5-1

SC-6-1

Hydrogenation step (S/C=500): In an argon-filled glove box, f-amphox (55.2 mg, 0.1 mmol) and a metal precursor $[Ir(COD)Cl]_2$ (33.5 mg, 0.5 mmol) were dissolved in anhydrous and anaerobic i-PrOH (1 mL), and stirred at room temperature for 1 hr, to obtain a catalyst solution of 100 μmol/mL. In the glove box, Compound SC-5-1 (3.28 g, 20 mmol) was dissolved in a 100 mL reaction flask containing 50 mL of anhydrous and anaerobic isopropanol, then $K_2CO_3$ (27.8 mg, 0.01 mmol) was added to the reaction system, and finally 0.4 mL of the fresh catalyst prepared above was added. The reaction flask was transferred to a hydrogenation reactor, and the reactor was purged three times with hydrogen and then introduced with 50 atm of hydrogen. The reaction system was stirred 24 hrs at room temperature. After the reaction, hydrogen in the reactor was discharged, and the reaction solution was dried by rotary evaporation. The obtained crude product was subjected to silica gel column chromatography with eluent of petroleum ether: ethyl acetate=2:1, to obtain 3.2 g of a liquid product SC-6-1 as a light yellow oil (yield 98%).

$^1$H NMR (400 MHz, $CDCl_3$) δ 7.34-7.25 (m, 2H), 7.19 (dd, J=10.6, 4.3 Hz, 3H), 3.72 (tdd, J=7.8, 5.0, 3.1 Hz, 1H), 3.55 (ddd, J=18.8, 11.1, 5.3 Hz, 2H), 2.96-2.62 (m, 4H), 1.84-1.66 (m, 2H). $^{13}$C NMR (101 MHz, $CDCl_3$) δ 141.64 (s), 128.42 (s), 128.37 (s), 125.93 (s), 71.52 (s), 66.74 (s), 34.61 (s), 31.76 (s).
Step 2:

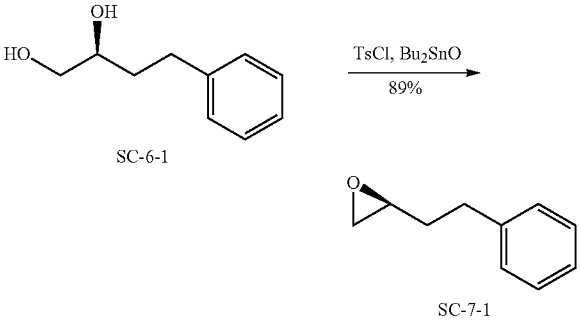

SC-6-1

SC-7-1

$^1$H NMR (400 MHz, $CDCl_3$) δ 7.31-7.23 (m, 2H), 7.17 (dd, J=10.7, 4.4 Hz, 3H), 2.92 (dddd, J=6.5, 5.0, 4.0, 2.8 Hz, 1H), 2.85-2.68 (m, 3H), 2.44 (dd, J=5.0, 2.7 Hz, 1H), 1.92-1.74 (m, 2H). $^{13}$C NMR (101 MHz, $CDCl_3$) δ 141.12 (s), 128.29 (s), 128.23 (s), 125.87 (s), 51.60 (s), 47.05 (s), 34.15 (s), 32.10 (s).
Step 3:

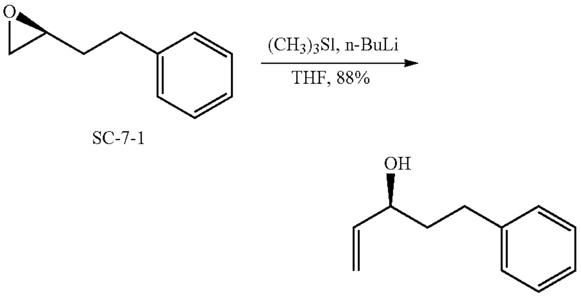

SC-7-1

SC-8-1

Under an argon atmosphere at −20° C., $(Me)_3S1$ (30 g, 147 mmol) and 100 mL of anhydrous THF were added to a 250 mL dry reaction flask, and then 61.2 mL (2.4 M, 147 mmol) of n-butyl lithium was added dropwise to the reaction solution, and reacted at −20° C. for 30 minutes. Compound SC-7-1 (4.35, 29.3 mmol) was dissolved in 10 mL of dry THF, and slowly added dropwise to the above reaction solution. The reaction solution was then slowly heated to room temperature, and continuously reacted for 5 hrs. The reaction was monitored by TLC. After the reaction was completed, the reaction was terminated by adding a saturated ammonium chloride aqueous solution. The reaction solution was extracted with ethyl acetate (100 mL*3), and the organic phases were combined, and dried with anhydrous sodium sulfate by rotary evaporation. The obtained crude product was subjected to silica gel column chromatography with eluent of petroleum ether:ethyl acetate=20:1, to obtain 4.0 g of a liquid product SC-8-1 as a light yellow oil (yield 85%).

$^1$H NMR (400 MHz, $CDCl_3$) δ 7.34-7.27 (m, 2H), 7.25-7.18 (m, 3H), 5.92 (ddd, J=17.0, 10.4, 6.2 Hz, 1H), 5.38-5.07 (m, 2H), 4.14 (q, J=6.1 Hz, 1H), 2.85-2.62 (m, 2H), 1.95-1.83 (m, 2H). $^{13}$C NMR (101 MHz, $CDCl_3$) δ 141.81 (s), 140.93 (s), 128.41 (s), 128.35 (s), 125.80 (s), 114.91 (s), 72.42 (s), 38.44 (s), 31.57 (s).

Example 7

The preparation method of another specific intermediate in Example 4 was as follows:
Step 1:

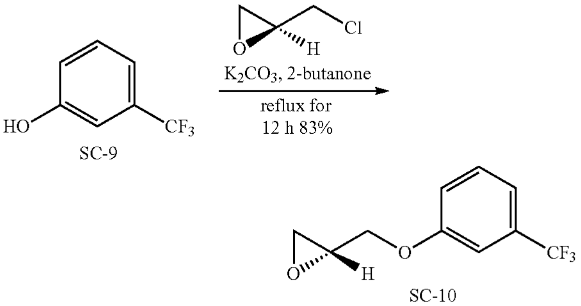

SC-9

SC-10

At room temperature, Compound SC-9 (100 g, 617 mmol) and 700 mL of 2-butanone were added to a 1000 mL dry reaction flask, and then epichlorohydrin (143 g, 1.5 mol) and anhydrous potassium carbonate (170 g, 1234 mmol) were added to the reaction solution. The reaction solution was heated to reflux for 12 hrs. Then, water was added to stop the reaction. The reaction solution was extracted with ethyl acetate (200 mL*3), and the organic phases were combined, and dried with anhydrous sodium sulfate by rotary evaporation. The obtained crude product was subjected to silica gel column chromatography with eluent of petroleum ether: ethyl acetate=20:1, to obtain 112 g of a liquid product as a light SC-10 yellow oil (512 mmol, yield 85%).

$^1$H NMR (600 MHz, $CDCl_3$) δ 7.36 (t, J=8.0 Hz, 1H), 7.19 (d, J=7.7 Hz, 1H), 7.13 (s, 1H), 7.07 (d, J=8.3 Hz, 1H), 4.26 (dd, J=11.0, 2.7 Hz, 1H), 3.98-3.87 (m, 1H), 3.33 (dt, J=5.8, 2.9 Hz, 1H), 2.86 (dt, J=19.1, 4.4 Hz, 1H), 2.73 (dd, J=4.4, 2.8 Hz, 1H). $^{13}$C NMR (151 MHz, $CDCl_3$) δ 170.97 (s), 158.53 (s), 131.76 (q, J=32.2 Hz), 129.96 (s), 123.82 (q, J=272.3 Hz), 118.04 (s), 117.76 (q, J=3.5 Hz), 111.37 (d, J=3.9 Hz), 68.98 (s), 60.22 (s), 49.79 (s), 44.31 (s), 20.81 (s), 14.01 (s).

Step 2:

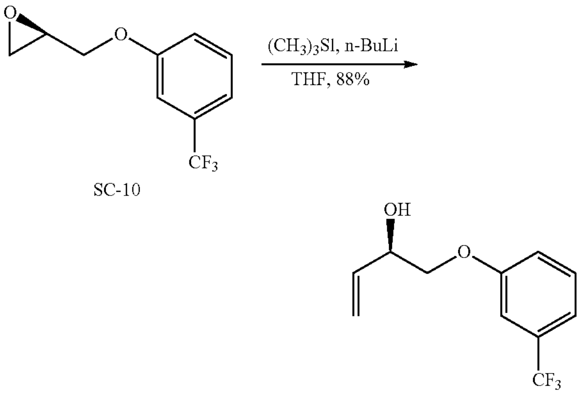

SC-10

SC-11

Under an argon atmosphere at −20° C., $(Me)_3S1$ (30 g, 147 mmol) and 100 mL of anhydrous THF were added to a 250 mL dry reaction flask, and then 61.2 mL (2.4 M, 147 mmol) of n-butyl lithium was added dropwise to the reaction solution, and reacted at −20° C. for 30 minutes. Compound SC-10 (6.38, 29.3 mmol) was dissolved in 10 mL of dry THF, and slowly added dropwise to the above reaction solution. The reaction solution was then slowly heated to room temperature, and continuously reacted for 5 hrs. The reaction was monitored by TLC. After the reaction was completed, the reaction was terminated by adding a saturated ammonium chloride aqueous solution. The reaction solution was extracted with ethyl acetate (100 mL*3), and the organic phases were combined, and dried with anhydrous sodium sulfate by rotary evaporation. The obtained crude product was subjected to silica gel column chromatography with eluent of petroleum ether:ethyl acetate=20:1, to obtain 6.17 g of a liquid product SC-11 as a light yellow oil (yield 85%).

$^1$H NMR (400 MHz, $CDCl_3$) δ 7.39 (t, J=8.0 Hz, 1H), 7.23 (d, J=7.7 Hz, 1H), 7.15 (s, 1H), 7.09 (dd, J=8.3, 2.4 Hz, 1H), 5.96 (ddd, J=17.2, 10.6, 5.7 Hz, 1H), 5.47 (dt, J=17.3, 1.4 Hz, 1H), 5.31 (dt, J=10.6, 1.3 Hz, 1H), 4.65-4.54 (m, 1H), 4.05 (dd, J=9.4, 3.4 Hz, 1H), 3.93 (dd, J=9.4, 7.5 Hz, 1H), 2.44 (d, J=3.9 Hz, 1H). $^{13}$C NMR (101 MHz, $CDCl_3$) δ 158.54 (s), 135.84 (s), 131.81 (q, J=32.4 Hz), 130.00 (s), 123.84 (q, J=272.3 Hz), 117.99 (s), 117.82 (q, J=3.8 Hz), 117.31 (s), 111.42 (q, J=3.8 Hz), 71.84 (s), 71.03 (s).

Example 8

The preparation method of another specific intermediate in Example 4 was as follows:

Step 1:

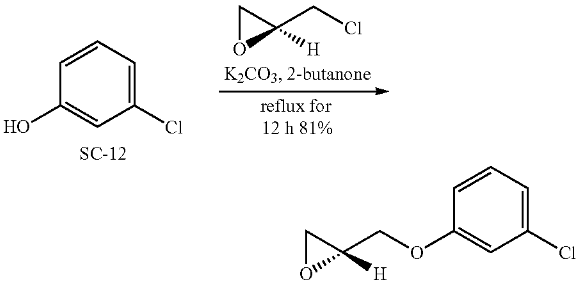

SC-12

SC-13

At room temperature, Compound SC-12 (2 g, 15.6 mmol) and 50 mL of 2-butanone were added to a 1000 mL dry reaction flask, and then epichlorohydrin (3.6 g, 39 mol) and anhydrous potassium carbonate (4.3 g, 31.2 mmol) were added to the reaction solution. The reaction solution was heated to reflux for 12 hrs. Then, water was added to stop the reaction. The reaction solution was extracted with ethyl acetate (50 mL*3), and the organic phases were combined, and dried with anhydrous sodium sulfate by rotary evaporation. The obtained crude product was subjected to silica gel column chromatography with eluent of petroleum ether: ethyl acetate=20:1, to obtain 2.3 g of a liquid product SC-13 as a light yellow oil (12.6 mmol, yield 81%).

$^1$H NMR (400 MHz, $CDCl_3$) δ 7.17 (t, J=8.1 Hz, 1H), 6.93 (ddd, J=7.9, 1.9, 0.9 Hz, 1H), 6.90 (t, J=2.2 Hz, 1H), 6.79 (ddd, J=8.4, 2.5, 0.8 Hz, 1H), 4.20 (dd, J=11.0, 2.9 Hz, 1H), 3.85 (dd, J=11.0, 5.9 Hz, 1H), 3.31 (ddt, J=5.7, 4.1, 2.8 Hz, 1H), 2.87 (dd, J=4.8, 4.2 Hz, 1H), 2.71 (dd, J=4.9, 2.7 Hz, 1H). $^{13}$C NMR (101 MHz, $CDCl_3$) δ 159.00 (s), 134.62 (s), 130.12 (s), 121.15 (s), 114.85 (s), 112.92 (s), 68.79 (s), 49.74 (s), 44.27 (s).

Step 2:

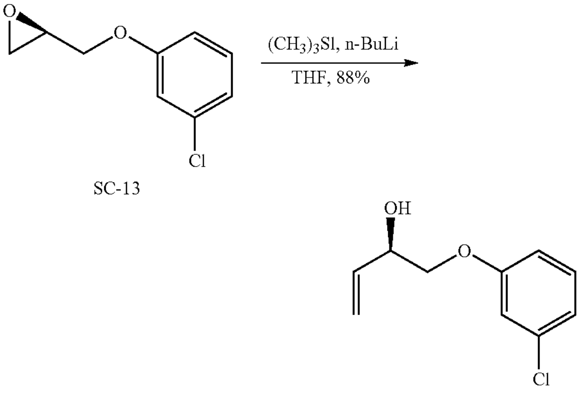

SC-13

SC-14

Under an argon atmosphere at −20° C., $(Me)_3SI$ (30 g, 147 mmol) and 100 mL of anhydrous THF were added to a 250 mL dry reaction flask, and then 61.2 mL (2.4 M, 147 mmol) of n-butyl lithium was added dropwise to the reaction solution, and reacted at −20° C. for 30 minutes. Compound SC-13 (5.4 g, 29.3 mmol) was dissolved in 10 mL of dry THF, and slowly added dropwise to the above reaction solution. The reaction solution was then slowly heated to room temperature, and continuously reacted for 5 hrs. The reaction was monitored by TLC. After the reaction was completed, the reaction was terminated by adding a saturated ammonium chloride aqueous solution. The reaction solution was extracted with ethyl acetate (100 mL*3), and the organic phases were combined, and dried with anhydrous sodium sulfate by rotary evaporation. The obtained crude product was subjected to silica gel column chromatography with eluent of petroleum ether:ethyl acetate=20:1, to obtain 4.95 g of a liquid product SC-14 as a light yellow oil (yield 85%).

$^1H$ NMR (400 MHz, $CDCl_3$) δ 7.19 (t, J=8.1 Hz, 1H), 6.95 (ddd, J=7.9, 1.9, 0.8 Hz, 1H), 6.91 (t, J=2.2 Hz, 1H), 6.80 (ddd, J=8.4, 2.4, 0.8 Hz, 1H), 5.93 (ddd, J=17.2, 10.6, 5.6 Hz, 1H), 5.45 (dt, J=17.3, 1.4 Hz, 1H), 5.29 (dt, J=10.6, 1.3 Hz, 1H), 4.66-4.49 (m, 1H), 3.99 (dd, J=9.4, 3.5 Hz, 1H), 3.87 (dd, J=9.4, 7.6 Hz, 1H), 2.58 (d, J=3.7 Hz, 1H). $^{13}C$ NMR (101 MHz, $CDCl_3$) δ 159.10 (s), 135.80 (s), 134.83 (s), 130.23 (s), 121.36 (s), 117.31 (s), 115.01 (s), 113.03 (s), 71.80 (s), 71.00 (s).

Example 9

Preparation of Prostaglandin Compound $PGF_{2\alpha}$

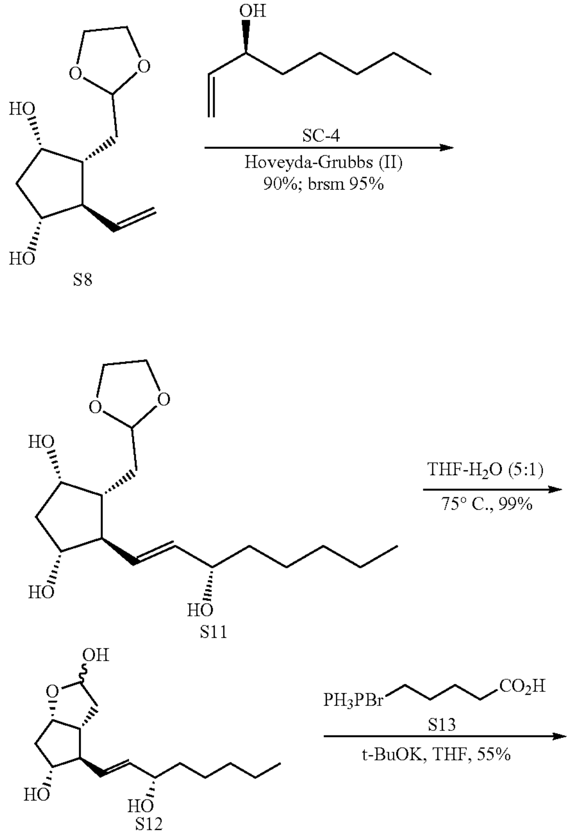

S8

S11

S12

-continued

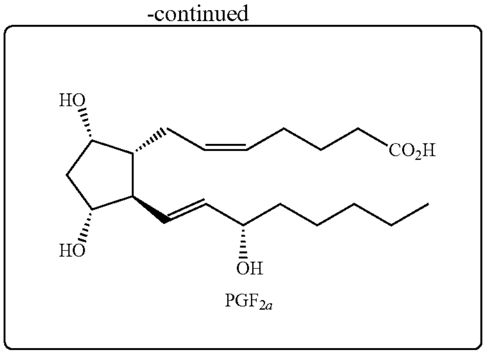

$PGF_{2\alpha}$

Step 1:

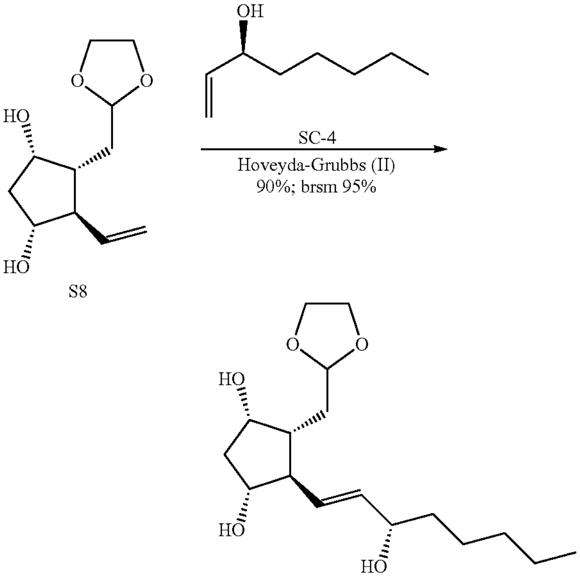

S8

S11

In an argon-filled glove box, Compound S8 (22 mg, 0.1 mmol), SC-4 (65.5 mg, 0.5 mmol) and second-generation Hovedy-Grubbs catalyst (6.2 mg, 0.01 mmol) were dissolved in anhydrous and anaerobic DCM (2 mL). Then the reaction system was heated to 60° C. and stirred for 5 hrs. The reaction was monitored by TLC. After the reaction was completed, the reaction solution was dried by rotary evaporation. The obtained crude product was subjected to silica gel column chromatography with eluent of petroleum ether: ethyl acetate=1:1, to obtain 27 mg of a liquid product S11 as a light yellow oil (yield 95%), and 6 mg of raw material was recovered.

$^1H$ NMR (600 MHz, $CDCl_3$) δ 5.55 (dd, J=15.2, 7.3 Hz, 1H), 5.41 (dd, J=15.2, 9.1 Hz, 1H), 4.89 (t, J=4.0 Hz, 1H), 4.20 (s, 1H), 4.07-3.98 (m, 2H), 3.96 (dd, J=10.8, 6.3 Hz, 1H), 3.86 (ddt, J=18.7, 12.2, 6.2 Hz, 3H), 3.13 (s, 2H), 2.44 (s, 1H), 2.37-2.28 (m, 1H), 2.25 (dd, J=17.1, 9.8 Hz, 1H), 1.92 (s, 1H), 1.87-1.81 (m, 2H), 1.73-1.64 (m, 2H), 1.59-1.51 (m, 1H), 1.50-1.41 (m, 1H), 1.39-1.23 (m, 6H), 0.87 (t, J=6.7 Hz, 3H). $^{13}C$ NMR (151 MHz, $CDCl_3$) δ 136.01 (s), 132.15 (s), 103.81 (s), 77.15 (s), 72.96 (s), 71.96 (s), 65.16 (s), 64.61 (s), 55.82 (s), 44.87 (s), 41.80 (s), 37.20 (s), 31.70 (s), 31.07 (s), 25.19 (s), 22.57 (s), 13.99 (s).

Step 2:

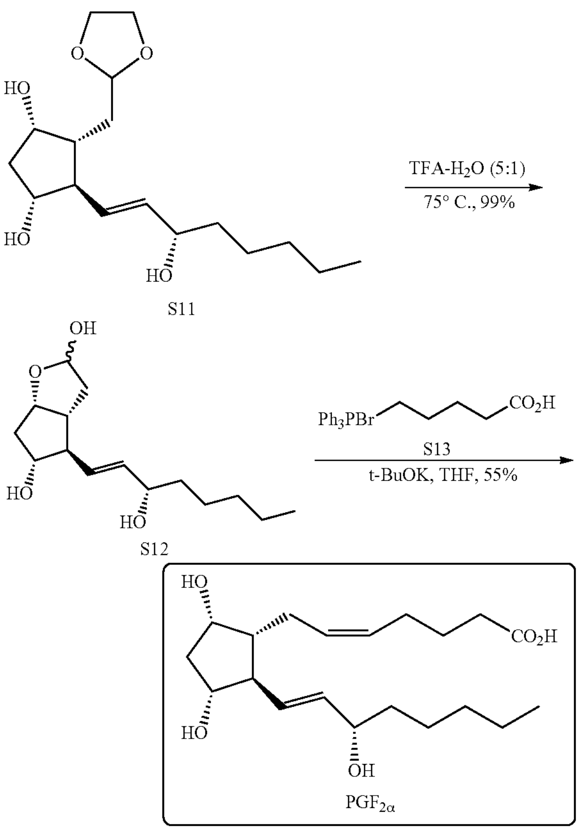

S11

S12

$PGF_{2\alpha}$

Compound S11 (35 mg, 0.11 mmol), 5 mL of THF and 1 mL of deionized water were added to a 25 mL reaction flask, and then TsOH (1.7 mg, 0.01 mmol) was added to the reaction solution in one portion, and reacted at 75° C. for 3 hrs. The reaction was monitored by TLC. After the reaction was completed, the reaction was terminated by adding a saturated sodium bicarbonate aqueous solution. The reaction solution was extracted with ethyl acetate (5 mL*3), and the organic phases were combined, and dried with anhydrous sodium sulfate by rotary evaporation. The obtained crude product S12 was directly used in the next reaction. Under an argon atmosphere at −78° C., Compound S13 (243 mg, 0.55 mmol) and 5 mL of anhydrous THF were added to a 25 mL dry reaction flask, and then 1.1 mL (1 M, 1.1 mmol) of n-butyl lithium was added dropwise to the reaction solution, and reacted at −78° C. for 30 minutes. Then the freshly prepared compound S12 above was dissolved in 2 mL of dry THF, and slowly added dropwise to the above reaction solution. The reaction solution was then heated to room temperature, and continuously reacted for 2 hrs. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 21 mg of a liquid product $PG_{2\alpha}$ as a light yellow oil (yield of two steps: 55%).

$^1H$ NMR (600 MHz, $CDCl_3$) δ 5.56 (dd, J=15.3, 7.0 Hz, 1H), 5.46 (ddd, J=19.9, 14.7, 8.0 Hz, 2H), 5.40-5.30 (m, 1H), 4.29 (s, 3H), 4.16 (s, 1H), 4.08 (dt, J=16.4, 8.2 Hz, 1H), 3.94 (s, 1H), 2.33 (t, J=6.4 Hz, 3H), 2.28-2.17 (m, 2H), 2.11 (dd, J=13.1, 6.9 Hz, 3H), 1.74 (d, J=14.6 Hz, 1H), 1.67 (dd, J=16.9, 13.0 Hz, 2H), 1.61-1.53 (m, 1H), 1.46 (dt, J=26.4, 8.9 Hz, 2H), 1.39-1.22 (m, 8H), 0.88 (t, J=6.7 Hz, 3H). $^{13}C$ NMR (151 MHz, $CDCl_3$) δ 134.91 (s), 132.63 (s), 129.61 (s), 129.16 (s), 77.68 (s), 73.12 (s), 72.57 (s), 55.38 (s), 50.30 (s), 42.72 (s), 36.94 (s), 32.99 (s), 31.71 (s), 26.27 (s), 25.22 (s), 24.51 (s), 22.61 (s), 14.02 (s).

Example 10

Preparation of Prostaglandin Compound Travoprost:

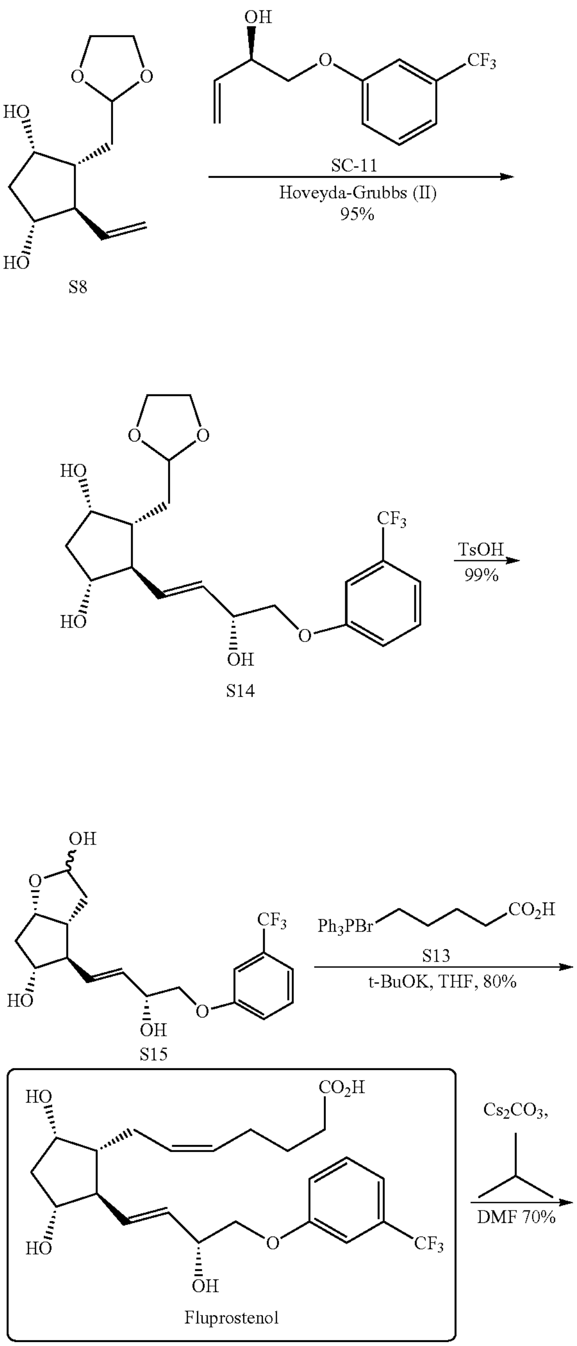

S8

S14

S15

Fluprostenol

-continued

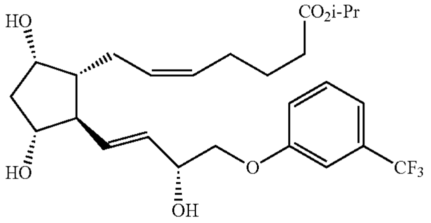

Travoprost

Step 1:

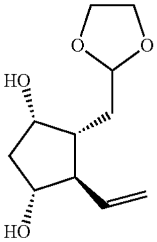

S8

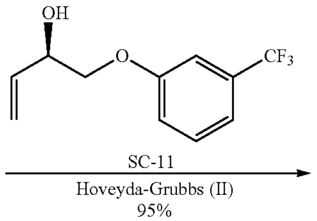

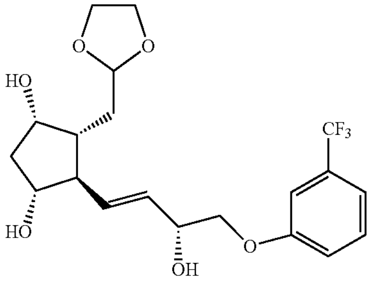

S14

In an argon-filled glove box, Compound S8 (43 mg, 0.2 mmol), SC-11 (243 mg, 1.0 mmol) and second-generation Hovedy-Grubbs catalyst (12 mg, 0.02 mmol) were dissolved in anhydrous and anaerobic DCM (2 mL). Then the reaction system was heated to 60° C. and stirred for 5 hrs. The reaction was monitored by TLC. After the reaction was completed, the reaction solution was dried by rotary evaporation. The obtained crude product was subjected to silica gel column chromatography with eluent of petroleum ether: ethyl acetate=1:1, to obtain 68 mg of a liquid product S14 as a light yellow oil (yield 82%).

$^1$H NMR (400 MHz, $CDCl_3$) δ 7.36 (t, J=8.0 Hz, 1H), 7.19 (d, J=7.7 Hz, 1H), 7.13 (s, 1H), 7.06 (dd, J=8.3, 2.0 Hz, 1H), 5.73-5.62 (m, 2H), 4.87 (dd, J=4.7, 3.1 Hz, 1H), 4.51 (d, J=3.4 Hz, 1H), 4.20 (s, 1H), 4.06-3.75 (m, 7H), 3.37-3.18 (m, 3H), 2.29 (dt, J=8.0, 6.8 Hz, 2H), 1.95-1.78 (m, 2H), 1.77-1.65 (m, 2H). $^{13}$C NMR (101 MHz, $CDCl_3$) δ 158.59 (s), 133.88 (s), 131.76 (q, J=32.3 Hz), 130.08 (s), 129.98 (s), 123.84 (q, J=272.3 Hz), 117.94 (s), 117.70 (q, J=3.6 Hz), 111.51 (q, J=3.8 Hz), 103.66 (s), 77.09 (s), 72.01 (d, J=3.6 Hz), 70.19 (s), 65.10 (s), 64.54 (s), 55.79 (s), 44.82 (s), 41.83 (s), 30.98 (s).

Step 2:

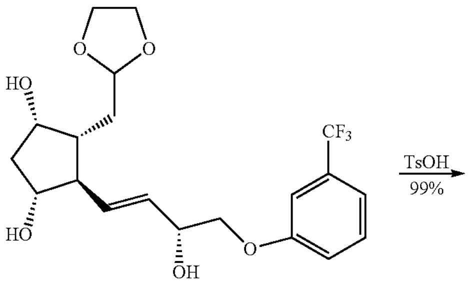

S14

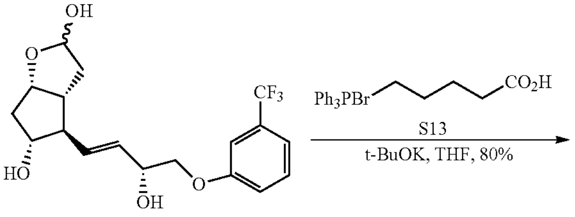

S15

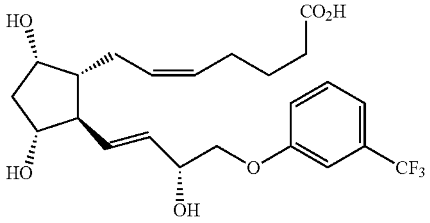

Fluprostenol

Compound S14 (46 mg, 0.11 mmol), 5 mL of THF and 1 mL of deionized water were added to a 25 mL reaction flask, and then TsOH (1.9 mg, 0.015 mmol) was added to the reaction solution in one portion, and reacted at 75° C. for 3 hrs. The reaction was monitored by TLC. After the reaction was completed, the reaction was terminated by adding a saturated sodium bicarbonate aqueous solution. The reaction solution was extracted with ethyl acetate (5 mL*3), and the organic phases were combined, and dried with anhydrous sodium sulfate by rotary evaporation. The obtained S15 crude product was directly used in the next reaction. Under an argon atmosphere at −78° C., Compound S13 (243 mg, 0.55 mmol) and 5 mL of anhydrous THF were added to a 25 mL dry reaction flask, and then 1.1 mL (1 M, 1.1 mmol) of n-butyl lithium was added dropwise to the reaction solution, and reacted at −78° C. for 30 minutes. Then the freshly prepared compound S15 above was dissolved in 2 mL of dry THF, and slowly added dropwise to the above reaction solution. The reaction was then heated to room temperature, and continuously reacted for 2 hrs. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 40 mg of a liquid product Fluprostenol as a light yellow oil (yield of two steps: 80%).

$^1$H NMR (600 MHz, $CDCl_3$) δ 7.40 (t, J=8.0 Hz, 1H), 7.23 (d, J=7.7 Hz, 1H), 7.15 (s, 1H), 7.09 (dd, J=8.3, 2.3 Hz, 1H), 5.71 (ddd, J=21.7, 15.3, 7.6 Hz, 2H), 5.52 (dd, J=17.7, 7.7 Hz, 1H), 5.40 (dd, J=18.3, 7.8 Hz, 1H), 4.60 (td, J=7.2, 3.3 Hz, 1H), 4.24 (s, 1H), 4.09-3.95 (m, 3H), 2.77 (s, 4H), 2.43-2.23 (m, 5H), 2.20-2.04 (m, 5H), 1.82 (d, J=14.7 Hz, 1H), 1.66 (ddt, J=26.6, 13.7, 7.0 Hz, 2H), 1.55-1.48 (m, 1H). $^{13}C$ NMR (151 MHz, $CDCl_3$) δ 158.49 (s), 135.95 (s), 131.95 (q, J=32.2 Hz), 130.10 (s), 129.84 (s), 128.81 (s), 128.78 (s), 126.66-120.94 (m), 118.08 (s), 117.99 (q, J=3.5 Hz), 111.51 (d, J=3.6 Hz), 78.00 (s), 72.86 (s), 71.82 (s), 71.18 (s), 56.33 (s), 51.17 (s), 43.17 (s), 32.56 (s), 29.69 (s), 26.12 (s), 25.07 (s), 24.49 (s).

Example 11

Method for preparing Travoprost with Compound Fluprostenol:

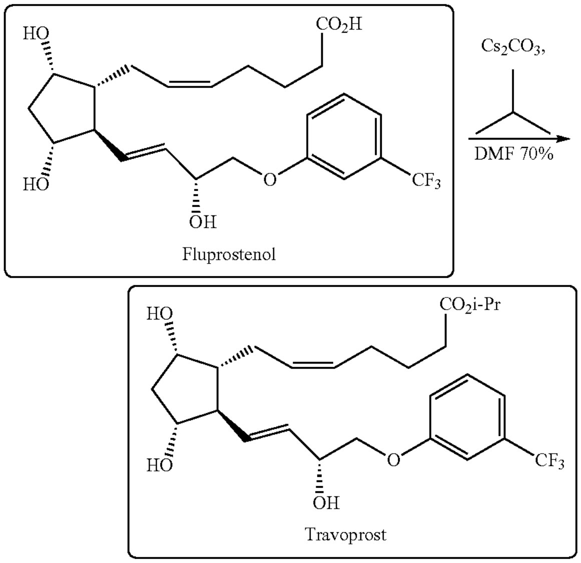

Fluprostenol

Travoprost

Fluprostenol (20 mg, 0.043 mmol) and 2 mL of DMF were added to a 25 mL reaction flask, and then $CsCO_3$ (21.1 mg, 0.065 mmol) was added to the reaction solution in one portion, and reacted at room temperature for 24 hrs. The reaction was monitored by TLC. After the reaction was completed, water was added to stop the reaction. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=8:1, to obtain 18 mg of a liquid product Travoprost as a light yellow oil (yield 86%).

$^{1}H$ NMR (400 MHz, $CDCl_3$) δ 7.39 (t, J=8.0 Hz, 1H), 7.22 (d, J=7.7 Hz, 1H), 7.15 (s, 1H), 7.09 (dd, J=8.3, 2.2 Hz, 1H), 5.83-5.62 (m, 2H), 5.52-5.34 (m, 2H), 4.99 (hept, J=6.3 Hz, 1H), 4.54 (dd, J=10.8, 5.3 Hz, 1H), 4.21 (d, J=2.9 Hz, 1H), 4.07-3.89 (m, 3H), 2.71 (d, J=3.7 Hz, 1H), 2.48 (d, J=6.5 Hz, 1H), 2.40 (ddd, J=10.4, 8.6, 4.7 Hz, 1H), 2.35-2.24 (m, 4H), 2.21-2.04 (m, 4H), 1.82 (dd, J=14.5, 2.0 Hz, 1H), 1.73-1.62 (m, 3H), 1.57 (ddd, J=14.8, 10.3, 4.4 Hz, 1H), 1.22 (dt, J=6.3, 3.0 Hz, 6H). $^{13}C$ NMR (101 MHz, $CDCl_3$) δ 173.59 (s), 158.62 (s), 134.86 (s), 131.89 (q, J=32.3 Hz), 130.04 (s), 129.89 (s), 129.34 (s), 128.93 (s), 123.86 (q, J=272.4 Hz), 118.05 (s), 117.84 (dd, =7.7, 3.8 Hz), 111.45 (q, J=3.8 Hz), 78.25 (s), 73.11 (s), 72.10 (s), 70.67 (s), 67.76 (s), 56.16 (s), 50.76 (s), 42.98 (s), 33.92 (s), 26.57 (s), 25.57 (s), 24.81 (s), 21.81 (s).

Example 12

Preparation of Prostaglandin Compound Cloprostenol:

The reaction route was shown below:

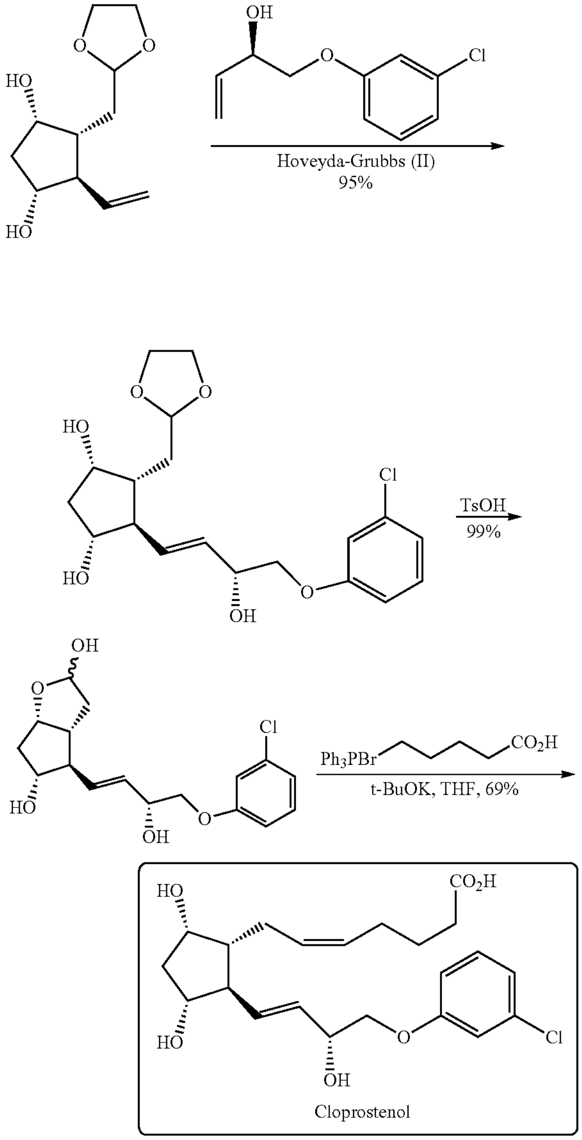

Cloprostenol

Step 1:

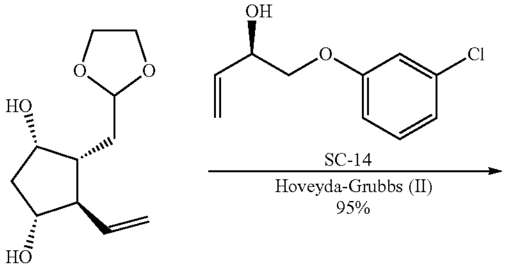

S8

-continued

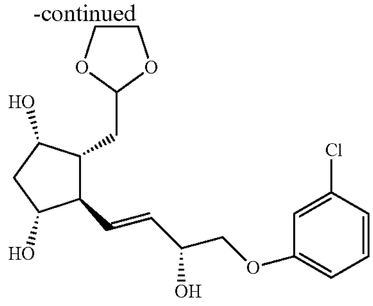

S16

-continued

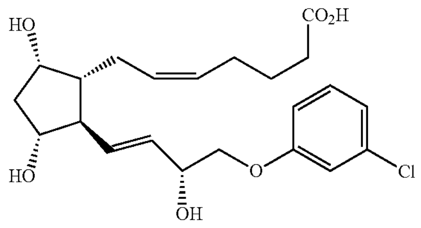

Cloprostenol

In an argon-filled glove box, Compound S8 (22 mg, 0.1 mmol), SC-14 (97 mg, 0.5 mmol) and second-generation Hovedy-Grubbs catalyst (6 mg, 0.01 mmol) were dissolved in anhydrous and anaerobic DCM (2 mL). Then the reaction system was heated to 60° C. and stirred for 5 hrs. The reaction was monitored by TLC. After the reaction was completed, the reaction solution was dried by rotary evaporation. The obtained crude product was subjected to silica gel column chromatography with eluent of petroleum ether: ethyl acetate=1:1, to obtain 35 mg of a liquid product S16 as a light yellow oil (yield 86%).

1H NMR (600 MHz, $CDCl_3$) δ 7.17 (q, J=7.8 Hz, 1H), 6.96-6.85 (m, 2H), 6.79 (dd, J=8.3, 2.3 Hz, 1H), 5.73-5.58 (m, 2H), 4.88 (dd, J=5.0, 2.9 Hz, 1H), 4.57-4.44 (m, 1H), 4.21 (s, 1H), 4.04-3.98 (m, 1H), 3.98-3.92 (m, 2H), 3.90-3.81 (m, 4H), 3.24 (d, J=35.0 Hz, 1H), 3.10 (s, 2H), 2.30 (qd, J=14.1, 8.5 Hz, 2H), 1.97-1.80 (m, 2H), 1.78-1.67 (m, 2H). $^{13}C$ NMR (151 MHz, $CDCl_3$) δ 159.19 (s), 134.81 (s), 133.88 (s), 130.22 (s), 130.06 (s), 121.26 (s), 115.10 (s), 113.03 (s), 103.69 (s), 77.14 (s), 72.09 (s), 71.99 (s), 70.23 (s), 65.12 (s), 64.57 (s), 55.86 (s), 44.89 (s), 41.84 (s), 31.03 (s).

Step 2:

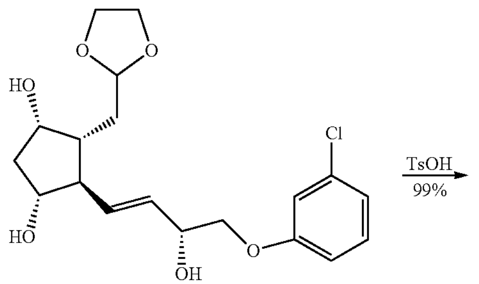

S16

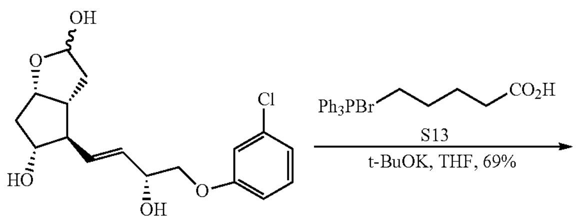

S17

Compound S16 (45 mg, 0.11 mmol), 5 mL of THF and 1 mL of deionized water were added to a 25 mL reaction flask, and then TsOH (2.58 mg, 0.015 mmol) was added to the reaction solution in one portion, and reacted at 75° C. for 3 hrs. The reaction was monitored by TLC. After the reaction was completed, the reaction was terminated by adding a saturated sodium bicarbonate aqueous solution. The reaction solution was extracted with ethyl acetate (5 mL*3), and the organic phases were combined, and dried with anhydrous sodium sulfate by rotary evaporation. The obtained crude product S17 was directly used in the next reaction. Under an argon atmosphere at −78° C., Compound S13 (243 mg, 0.55 mmol) and 5 mL of anhydrous THF were added to a 25 mL dry reaction flask, and then 1.1 mL (1 M, 1.1 mmol) of n-butyl lithium was added dropwise to the reaction solution, and reacted at −78° C. for 30 minutes. Then the freshly prepared compound S17 above was dissolved in 2 mL of dry THF, and slowly added dropwise to the above reaction solution. The reaction solution was then heated to room temperature, and continuously reacted for 2 hrs. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 34 mg of a liquid product Cloprostenol as a light yellow oil (yield of two steps: 69%).

$^1H$ NMR (600 MHz, $CDCl_3$) δ 7.20 (t, J=8.1 Hz, 1H), 6.97-6.94 (m, 1H), 6.92 (s, 1H), 6.81 (dd, J=8.3, 2.3 Hz, 1H), 5.69 (ddd, J=21.6, 15.2, 7.5 Hz, 2H), 5.52 (dd, J=17.7, 7.4 Hz, 1H), 5.39 (dd, J=18.0, 7.9 Hz, 1H), 4.62-4.53 (m, 1H), 4.23 (s, 1H), 4.10-3.96 (m, 2H), 3.93 (dd, J=22.7, 14.6 Hz, 1H), 2.82 (d, J=6.4 Hz, 4H), 2.36 (dd, J=18.9, 14.2 Hz, 3H), 2.30-2.23 (m, 1H), 2.21-2.05 (m, 4H), 1.81 (d, J=14.4 Hz, 1H), 1.66 (tt, J=20.8, 6.8 Hz, 2H), 1.50 (dd, J=12.7, 8.8 Hz, 1H). $^{13}C$ NMR (151 MHz, $CDCl_3$) δ 177.21 (s), 159.18 (s), 134.92 (s), 134.83 (s), 130.28 (s), 129.65 (s), 129.52 (s), 128.97 (s), 121.32 (s), 115.12 (s), 113.10 (s), 77.56 (s), 72.50 (s), 71.78 (s), 70.72 (s), 55.49 (s), 50.52 (s), 42.86 (s), 32.82 (s), 26.20 (s), 25.04 (s), 24.44 (s).

Example 13

Preparation of Prostaglandin Compound Latanoprost

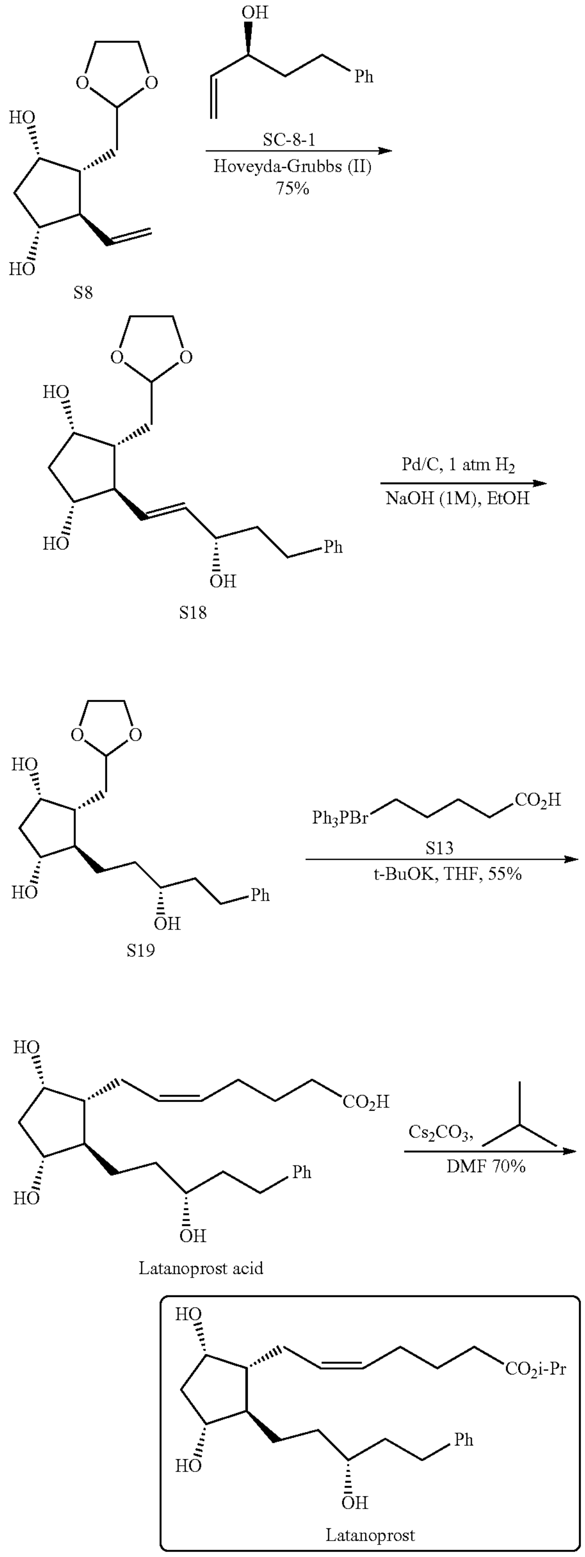

Step 1:

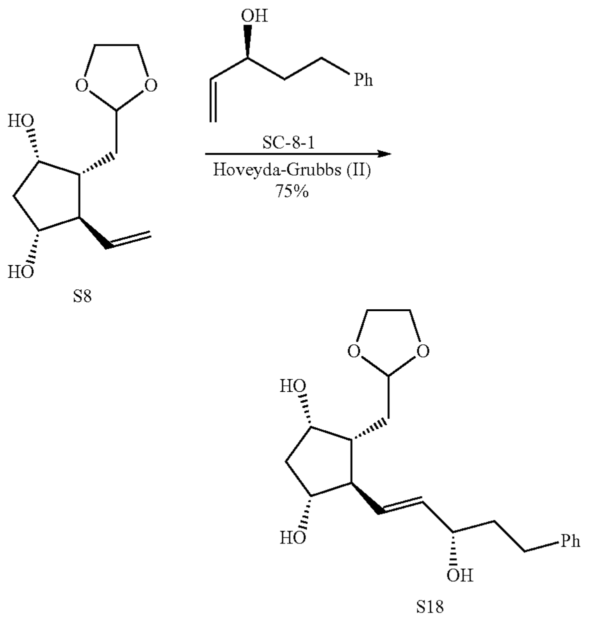 [SMILES: C=C[C@@H]1[C@@H](CC2OCCO2)[C@@H](O)C[C@H]1O ; C=C[C@@H](O)CCc1ccccc1 ; "SC-8-1" ; "S8" ; O[C@H](/C=C/[C@@H]1[C@@H](CC2OCCO2)[C@@H](O)C[C@H]1O)CCc1ccccc1 ; "S18"]

In an argon-filled glove box, Compound S8 (48 mg, 0.2 mmol), SC-8-1 (162 mg, 0.5 mmol) and second-generation Hovedy-Grubbs catalyst (12.5 mg, 0.02 mmol) were dissolved in anhydrous and anaerobic DCM (2 mL). Then the reaction system was heated to 60° C. and stirred for 5 hrs. The reaction was monitored by TLC. After the reaction was completed, the reaction solution was dried by rotary evaporation. The obtained crude product was subjected to silica gel column chromatography with eluent of petroleum ether: ethyl acetate=1:1, to obtain 54 mg of a liquid product S18 as a light yellow oil (yield 78%).

$^1H$ NMR (400 MHz, $CDCl_3$) δ 7.27 (dd, J=9.0, 5.9 Hz, 2H), 7.21-7.14 (m, 2H), 5.73-5.54 (m, 1H), 5.50-5.31 (m, 1H), 4.89 (t, J=3.8 Hz, 1H), 4.20 (s, 1H), 4.12-3.92 (m, 3H), 3.92-3.74 (m, 3H), 3.34 (d, J=58.2 Hz, 1H), 3.20 (s, 1H), 2.85 (s, 1H), 2.78-2.60 (m, 2H), 2.39-2.30 (m, 1H), 2.26 (dd, J=17.4, 9.9 Hz, 1H), 2.05 (s, 1H), 1.96-1.75 (m, 4H), 1.69 (ddt, J=15.2, 9.9, 4.9 Hz, 2H). $^{13}C$ NMR (101 MHz, $CDCl_3$) δ 141.91 (s), 135.97 (s), 132.74 (s), 128.42 (s), 128.29 (s), 125.71 (s), 103.68 (s), 76.76 (s), 72.24 (s), 71.56 (s), 65.10 (s), 64.57 (s), 55.43 (s), 44.36 (s), 41.74 (s), 38.66 (s), 31.80 (s), 30.84 (s).

Step 2:

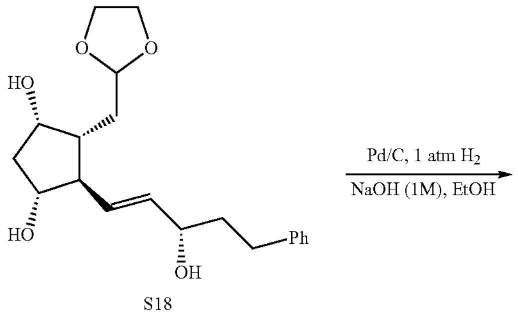

-continued

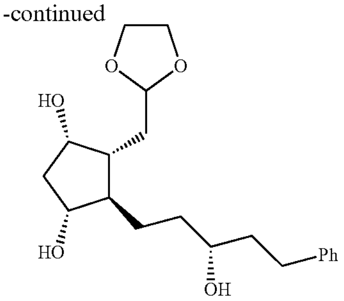

S19

Compound S18 (28 mg, 0.08 mmol), 10 mg of palladium on carbon, 2 mL of ethanol and 40 μl of sodium hydroxide aqueous solution (1.0 M, 40 μmol) were added to a 25 mL reaction flask, the reactor was purged three times with hydrogen and then introduced with 1 atm of hydrogen. The reaction was continued at room temperature for 5 hrs. The reaction was monitored by TLC. After the reaction was completed, the palladium on carbon was filtered off, and the solvent was removed by rotary evaporation. The obtained crude product S19 was directly used in the next reaction.

$^{1}$H NMR (600 MHz, $CDCl_3$) δ 7.20 (t, J=7.4 Hz, 2H), 7.15-7.08 (m, 3H), 4.84 (dd, J=13.3, 9.5 Hz, 1H), 4.15 (s, 1H), 3.99-3.86 (m, 2H), 3.86-3.74 (m, 3H), 3.65-3.51 (m, 1H), 3.13 (s, 2H), 2.81-2.66 (m, 1H), 2.65-2.52 (m, 1H), 1.94-1.78 (m, 4H), 1.71 (ddd, J=23.1, 11.7, 6.9 Hz, 2H), 1.66-1.58 (m, 1H), 1.56-1.45 (m, 3H), 1.38 (tt, J=19.2, 9.6 Hz, 1H), 1.29 (ddd, J=22.1, 14.6, 7.4 Hz, 1H). $^{13}$C NMR (151 MHz, $CDCl_3$) δ 142.08 (s), 128.37 (s), 128.36 (s), 125.75 (s), 103.81 (s), 78.17 (s), 74.35 (s), 71.20 (s), 65.10 (s), 64.58 (s), 53.32 (s), 46.83 (s), 41.66 (s), 39.04 (s), 35.57 (s), 32.86 (s), 32.07 (s), 29.35 (s).

Example 14

Preparation of Prostaglandin Compound Latanoprost

Step 1:

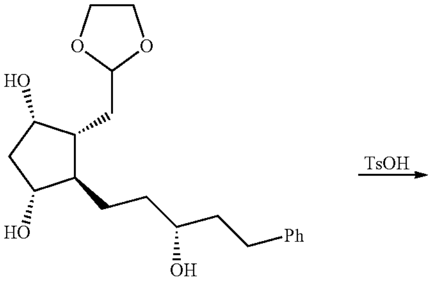

S19

-continued

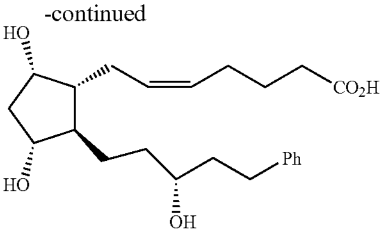

Latanoprost acid

Compound S19 (54 mg, 0.15 mmol), 5 mL of THF and 1 mL of deionized water were added to a 25 mL reaction flask, and then TsOH (2.5 mg, 0.015 mmol) was added to the reaction solution in one portion, and reacted at 75° C. for 3 hrs. The reaction was monitored by TLC. After the reaction was completed, the reaction was terminated by adding a saturated sodium bicarbonate aqueous solution. The reaction solution was extracted with ethyl acetate (5 mL*3), and the organic phases were combined, and dried with anhydrous sodium sulfate by rotary evaporation. The obtained crude product S20 was directly used in the next reaction. Under an argon atmosphere at −78° C., Compound S13 (332 mg, 0.75 mmol) and 5 mL of anhydrous THF were added to a 25 mL dry reaction flask, and then 1.5 mL (1 M, 1.5 mmol) of n-butyl lithium was added dropwise to the reaction solution, and reacted at −78° C. for 30 minutes. Then the freshly prepared compound S20 above was dissolved in 2 mL of dry THF, and slowly added dropwise to the above reaction solution. The reaction solution was then heated to room temperature, and continuously reacted for 2 hrs. The reaction was monitored by TLC. After the reaction was completed, the reaction was terminated by adding a saturated ammonium chloride aqueous solution. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 32 mg of a liquid product Latanoprost acid as a light yellow oil (yield of two steps: 55%).

$^{1}$H NMR (600 MHz, $CDCl_3$) δ 7.35-7.24 (m, 2H), 7.26-7.12 (m, 3H), 5.59-5.45 (m, 1H), 5.45-5.26 (m, 1H), 4.14 (d, J=23.8 Hz, 2H), 3.98-3.90 (m, 2H), 3.74-3.62 (m, 1H), 2.86-2.74 (m, 1H), 2.65 (ddd, J=19.4, 15.6, 9.5 Hz, 1H), 2.34 (dd, J=14.5, 7.8 Hz, 2H), 2.30-2.21 (m, 2H), 2.15 (td, J=14.9, 7.6 Hz, 2H), 1.93-1.82 (m, 2H), 1.81-1.74 (m, 2H), 1.73-1.65 (m, 3H), 1.61 (dd, J=13.8, 7.2 Hz, 2H), 1.53 (ddd, J=16.2, 12.0, 7.1 Hz, 1H), 1.40-1.30 (m, 2H). $^{13}$C NMR (151 MHz, $CDCl_3$) δ 177.26 (s), 142.05 (s), 129.45 (d, J=8.5 Hz), 128.40 (s), 125.82 (s), 78.55 (s), 74.43 (s), 71.52 (s), 52.39 (s), 51.66 (s), 42.48 (s), 38.73 (s), 35.19 (s), 33.04 (s), 32.08 (s), 29.04 (s), 26.63 (s), 26.35 (s), 24.63 (s).

Step 2:

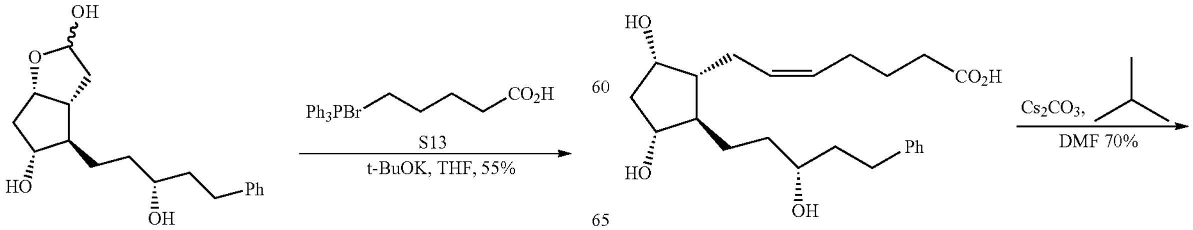

S20

Latanoprost acid

-continued

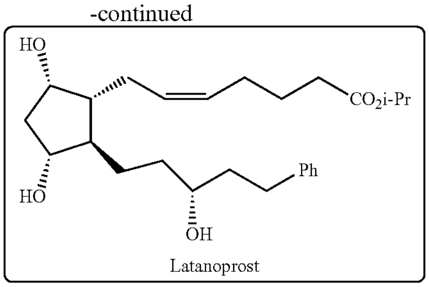

Latanoprost

Latanoprost acid (30 mg, 0.076 mmol) and 2 mL of DMF were added to a 25 mL reaction flask, and then $CsCO_3$ (37 mg, 0.114 mmol) was added to the reaction solution in one portion. The reaction was continued at room temperature for 24 hrs. The reaction was monitored by TLC. After the reaction was completed, water was added to stop the reaction. The reaction solution was extracted with ethyl acetate (5 mL*3), and the organic phases were combined, and dried with anhydrous sodium sulfate by rotary evaporation. The obtained crude product was subjected to silica gel column chromatography with eluent of petroleum ether:ethyl acetate=1:1, to obtain 24 mg of a liquid product Latanoprost as a light yellow oil (yield 73%).

$^1H$ NMR (600 MHz, $CDCl_3$) δ 7.24-7.18 (m, 2H), 7.17-7.08 (m, 3H), 5.39 (dt, J=10.8, 7.2 Hz, 1H), 5.31 (dt, J=18.0, 7.1 Hz, 1H), 5.02-4.88 (m, 1H), 4.09 (s, 1H), 3.89 (d, J=23.0 Hz, 1H), 3.66-3.54 (m, 1H), 2.77-2.68 (m, 1H), 2.66-2.57 (m, 1H), 2.44 (s, 1H), 2.29-2.19 (m, 3H), 2.14 (ddd, J=15.9, 11.5, 5.7 Hz, 1H), 2.06 (tq, J=14.5, 7.2 Hz, 2H), 1.85-1.75 (m, 3H), 1.75-1.68 (m, 2H), 1.65-1.58 (m, 3H), 1.57-1.51 (m, 2H), 1.50-1.42 (m, 1H), 1.36-1.24 (m, 2H), 1.19-1.11 (m, 6H). $^{13}C$ NMR (151 MHz, $CDCl_3$) δ 173.46 (s), 142.09 (s), 129.56 (s), 129.34 (s), 128.38 (s), 125.79 (s), 78.75 (s), 74.65 (s), 71.29 (s), 67.64 (s), 52.85 (s), 51.86 (s), 42.51 (s), 39.04 (s), 35.78 (s), 34.05 (s), 32.10 (s), 29.61 (s), 26.88 (s), 26.62 (s), 24.92 (s), 21.81 (s).

Referring to the aforementioned synthetic route, the intermediates can be used in the preparation of compounds shown in FIG. 1.

Preferred embodiments of the present invention have been described above. However, the present invention is not limited thereto. Any other changes, modifications, alternatives, combinations, simplifications made without departing from the spirit and principle of the present invention are all equivalent replacements, and fall in the protection scope of the present invention.

What is claimed is:

1. A key intermediate for synthesis of a prostaglandin compound, having a structure shown below:

I

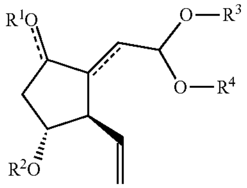

wherein ⎓ denotes a single bond or double bond, and if it is a double bond, $R^1$ is absent; and wherein $R^1$ and $R^2$ are each H or protecting groups; $R^3$ and $R^4$ are the same or different alkyl or aryl, or $R^3$ and $R^4$ form a ring.

2. The key intermediate for the synthesis of the prostaglandin compound according to claim 1, having a structure shown below:

Ia

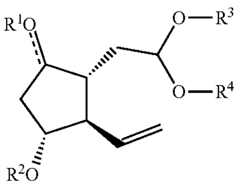

wherein $R^1$, $R^2$, $R^3$, and $R^4$ are as defined above.

3. The key intermediate for the synthesis of the prostaglandin compound according to claim 1, which is

1

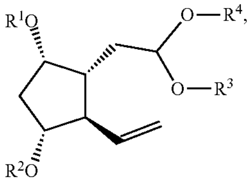

wherein $R^1$, $R^2$, $R^3$, and $R^4$ are as defined above.

4. The key intermediate for the synthesis of the prostaglandin compound according to claim 1, which is

7

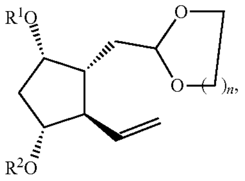

wherein $R^1$ and $R^2$ are as defined above, and n is an integer from 1 to 3.

5. The key intermediate for the synthesis of the prostaglandin compound according to claim 1, wherein the intermediate is

11

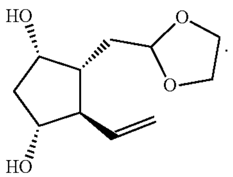

6. The key intermediate for the synthesis of the prostaglandin compound according to claim 1, wherein the protecting group is selected from an ether protecting group, an acyl protecting group, a silyl ether protecting group, an acetal protecting group.

7. The key intermediate for the synthesis of the prostaglandin compound according to claim 1, wherein the intermediate is selected from:

19

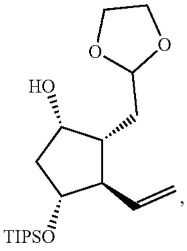

,

20

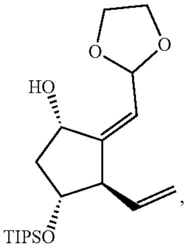

,

21

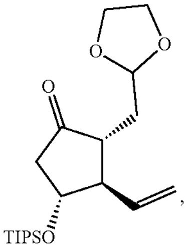

,

22

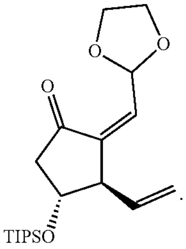

.

8. A method for preparing the key intermediate for the synthesis of the prostaglandin compound according to claim 1, comprising steps of:

a) asymmetrically reducing compound S1 to obtain chiral alcohol compound S2, and then protecting hydroxyl group of the chiral alcohol compound S2 with silane to obtain Weinreb amide compound S3;

b) subjecting the Weinreb amide compound S3 to an addition reaction with an alkyne reagent to obtain enyne compound S4;

c) subjecting the enyne compound S4 to a Zhang enyne cycloisomerization to obtain five-membered ring S5;

d) conjugating the five-membered ring S5 to reduce double bond thereof to obtain compound S6, and further reducing ketone of the compound S6 to obtain compound S7; and e) deprotecting the compound S7 by removing TIPS thereof to obtain compound S8;

referring to the following reaction route:

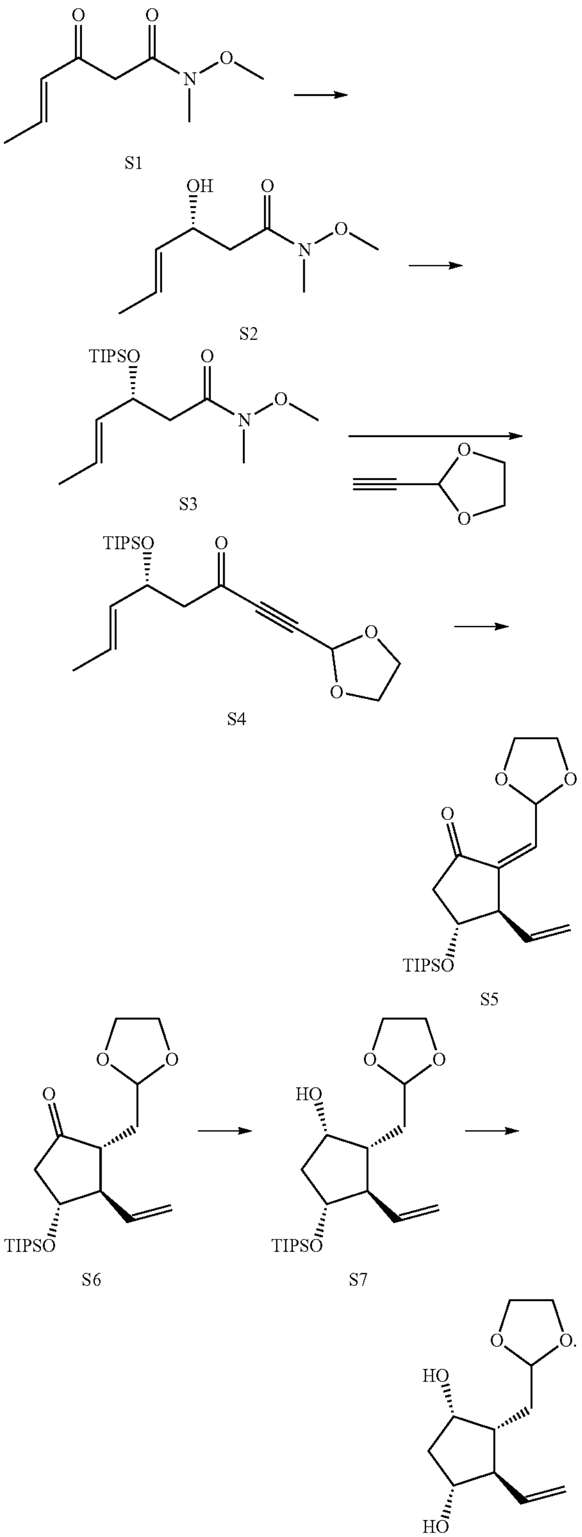

S1 S2 S3 S4 S5 S6 S7 S8

9. The key intermediate for the synthesis of the prostaglandin compound according to claim 1, having a structure shown below:

Ib

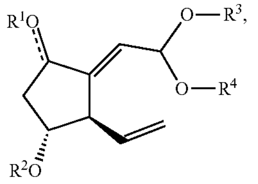

wherein $R^1$, $R^2$, $R^3$, and $R^4$ are as defined above.

10. The key intermediate for the synthesis of the prostaglandin compound according to claim 1, which is

2

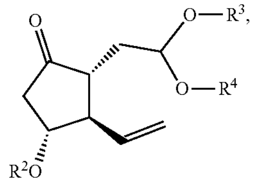

or

3

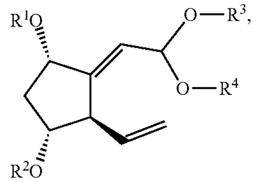

or

4

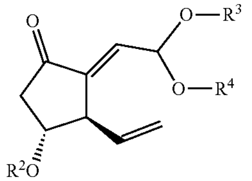

wherein $R^1$, $R^2$, $R^3$, and $R^4$ are as defined above.

11. The key intermediate for the synthesis of the prostaglandin compound according to claim 1, which is

8

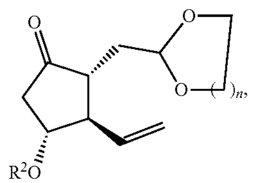

or

9

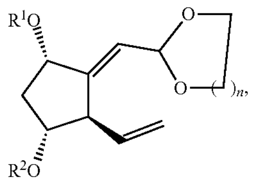

or

-continued

10

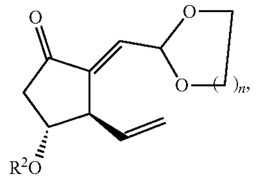

wherein $R^1$ and $R^2$ are as defined above, and n is an integer from 1 to 3.

12. The key intermediate for the synthesis of the prostaglandin compound according to claim 1, wherein the intermediate is selected from:

12

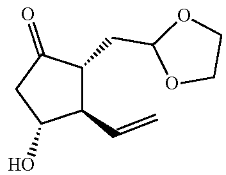

13

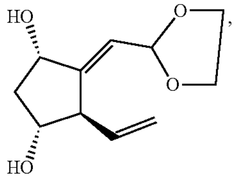

14

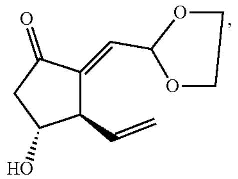

15

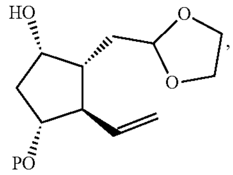

16

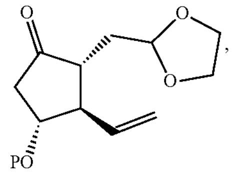

17

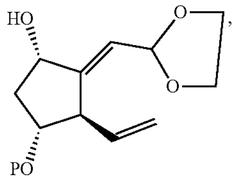

-continued
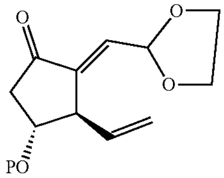
18
wherein P is a protecting group.
* * * * *